(12) United States Patent
Suzuki

(10) Patent No.: US 6,306,813 B1
(45) Date of Patent: Oct. 23, 2001

(54) ALKALINE LIPASE AND DETERGENT COMPOSITION ACTIVE AT LOW TEMPERATURE

(75) Inventor: Masahiro Suzuki, Nara (JP)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/142,785

(22) PCT Filed: Apr. 17, 1997

(86) PCT No.: PCT/DK97/00168

§ 371 Date: Sep. 11, 1998

§ 102(e) Date: Sep. 11, 1998

(87) PCT Pub. No.: WO97/40144

PCT Pub. Date: Oct. 30, 1997

(30) Foreign Application Priority Data

Apr. 18, 1996 (JP) ................................................ 8-096995

(51) Int. Cl.$^7$ ................................ C11D 3/386; C12N 9/20
(52) U.S. Cl. ........................ 510/392; 510/530; 510/226; 510/320; 510/321; 435/198
(58) Field of Search .............................. 435/198; 510/530, 510/226, 320, 321, 392

(56) References Cited

FOREIGN PATENT DOCUMENTS

| | | |
|---|---|---|
| 0 271 152 | 6/1988 | (EP) . |
| 0 375 102 | 6/1990 | (EP) . |
| WO 87/00859 | 2/1987 | (WO) . |
| WO 94/25578 | 11/1994 | (WO) . |
| WO 95/06720 | 3/1995 | (WO) . |
| 95/06720 | * 3/1995 | (WO) . |

OTHER PUBLICATIONS

Stepaniak et al., "Isolation and Partial Characterization of Heat Stable Proteinase, Lipase and Phospholipase C From Pseudomonas Fluorescens P1", Milchwissenschaft, vol. 42, No. 2, 1987, pp. 75–79.

Abstract No. 42063, B/22, Week 7922, Abstract of SU, 617473 (As USSR Microbiology Ins), Jul. 19, 1978.

* cited by examiner

*Primary Examiner*—Mark Kopec
*Assistant Examiner*—Charles Boyer
(74) *Attorney, Agent, or Firm*—Elias J. Lambiris, Esq.; Jason I. Garbell, Esq.

(57) ABSTRACT

Lipases having improved washing performance for use in detergents to improve the removal of fatty soiling, and having activity throughout a temperature range of 1 to 65° C., including an activity at 1° C. which is at least 20% the activity at 30° C., activity over a pH range of 8–12, and activity at high concentration of anionic surfactant and in the presence of bleach.

16 Claims, 8 Drawing Sheets

ALKALINE LIPASE AND DETERGENT COMPOSITION ACTIVE AT LOW TEMPERATURE

CROSS-REFERENCE TO RELATED APPLICATIONS

This application is a 35 U.S.C. 371 national application of PCT/DK97/00168 filed Apr. 17, 1998 and claims priority under 35 U.S.C. 119 of Japanese application 8/96995 filed Apr. 18, 1996, the contents of which are fully incorporated herein by reference.

FIELD OF THE INVENTION

This invention relates to a novel lipase, to a microorganism producing it, to a method for producing it and to its use. More particularly, this invention relates to a lipase which has effective activity in a detergent solution in the presence of a bleaching agent or at low temperature, to a method for producing such lipase, and to a detergent composition containing such lipase.

DESCRIPTION OF PRIOR ART

It is known to add a lipase to detergents so that lipids attached to an article to be cleaned can be decomposed and removed to increase washing efficiency. This use of lipases is described in, for example, H. Andree et al., "Lipase as detergent components," Journal of Applied Biochemistry, 2, 218–229 (1980).

Preferred lipases for detergent components are those which show sufficient lipase activity in washing solutions under washing conditions. Under ordinary washing conditions, the pH of washing solutions is in the alkaline region and, hence, lipases which act at alkaline pH values are desired. Generally, lipid stains can be removed relatively easily under conditions of high temperatures and high alkalinity. However, it is also known that such stains are difficult to remove by washing at low temperatures (i.e., from the temperature of tap water up to 40° C.) as is carried out in some countries such as Japan.

Washing temperature tends to be decreased in Europe as well as in Japan where mainly low temperature washing has been performed. Therefore, preferred lipases for detergent components are those which act sufficiently at low temperatures.

Further, preferred lipases for detergent components are those whose action is not inhibited in the presence of detergent components such as surfactants, proteases or bleaching agents contained in most of detergents and which exhibit sufficient effects with a single washing run. Furthermore, preferred lipases for detergent components are those which are stable when stored as blended in the detergents. There has been a keen desire for the development of detergent compositions containing lipases having the above-described preferred properties and having high washing effect.

Lipases are known to be produced by microorganisms belonging to the genera Pseudomonas, Alcaligenes, Achromobacter, Acinetobacter, Mucor, Candida, Humicola, Aspergillius, etc. However, most of the lipases produced by these microorganisms have optimum pH in the ranges of from neutral to weakly alkaline and, hence, the lipases do not act sufficiently in alkaline detergent solutions and have low stability in detergent solutions. Furthermore, some of these lipases are strongly inhibited in the presence of surfactants.

WO 87/00859 (Gist-Brocades) describes that some lipases produced by bacteria belonging to the genera Pseudomonas and Acinetobacter are effective in washing with anionic and nonionic detergents, respectively, and that such lipases are also effective in washing with a nonionic detergent containing a bleaching agent. However, the publication contains no mention of their effects in washing with anionic detergents containing a bleaching agent.

EP 271 152 (Unilever) discloses the use of a certain class of lipases together with strong bleaching agents in detergent compositions. The class of lipases includes, inter alia, some lipases from Pseudomonas.

WO 94/25578 (Genencor) discloses mutant enzymes of wild-type Pseudomonas pseudoalcaligenes lipase. The mutant enzymes have improved wash performance in a detergent which contains a bleaching agent.

Further, in those regions where people conduct washing at a tap water temperature without warming, e.g., in Japan, the washing temperature may be decreased sometimes, e.g., in winter season, to below 5° C. However, none of the above-described publications describes lipases which are sufficiently effective at low temperatures as low as below 5° C. nor detergent composition containing such lipases.

It is the object of this invention to provide a lipase having a sufficient washing effect at washing conditions used at present and in the future. More particularly, it is the object to provide a lipase which exhibits superior washing effect in detergents containing a bleaching agent or in washing at low temperatures.

STATEMENT OF THE INVENTION

With a view to overcoming the above-described problems, the present inventors have conducted screening by isolating and cultivating various microorganisms, and as a result they found that bacterial strains, representative examples of which include strains SD711, SD712, SD713, SD714, SD715, SD716, SD717, and SD718, can produce new lipases meeting the above-described requirements. Also, they have found that the lipases from these microorganisms share some characteristics which contribute to the washing performance and which known lipases do not share. This invention is achieved based on this discovery.

Accordingly, this invention provides a lipase having one or more of the following properties:

an optimum temperature of at least 40° C.

an activity at 1° C. which is at least 20% of the activity at 30° C.

an activity measured in a solution containing 0.02% sodium linear alkylbenzene sulfonate (LAS) using an olive oil emulsion as a substrate which is at least 20% of the activity in the absence of LAS a decomposition rate of p-nitrophenyl palmitate in a solution containing 0.046% LAS at 25° C. in the presence of 0.5% hydrogen peroxide of at least 80% of the decomposition rate in the absence of hydrogen peroxide a residual activity after incubation in a solution containing 0.05% LAS and 0.55% hydrogen peroxide at 25° C. for 1 hour, which is at least 50% of the activity before the incubation;

a decomposition rate of p-nitrophenyl palmitate in a solution at 25° C. containing 0.2% LAS which is at least 50% of the decomposition rate in a solution containing 0.02% LAS.

an optimum pH not lower than 11.

The invention also provides a bacterium capable of producing the lipase, a ethod for producing the lipase, and a detergent composition comprising the lipase.

DETAILED DESCRIPTION OF THE INVENTION

Hereafter, this invention will be described in detail.

Lipase-producing Microorganisms

Microorganisms which can be used for producing the lipase of this invention are not limited particularly. Such microorganisms can be selected from strain collections or newly isolated microorganisms occurring in nature, including spontaneous or artificial mutants of these strains, provided they have the ability to produce a lipase having the following characteristics.

Examples of bacterial strains belonging to the genus Pseudomonas which produce a lipase of this invention include strains SD711 to SD717 which the present inventors isolated from the soil. Bacterial characteristics of these strains were compared with similar *Pseudomonas stutzeri*, and *Pseudomonas mendocina, Pseudomonas alcaligenes, Pseudomonas pseudoalcaligenes* with reference to the literature ((1) Bergey's Manual of Determinative Bacteriology, Ninth Edition (1994) and (2) Bergey's Manual of Systematic Bacteriology, Vol. 1 (1984)) in Table 1, below.

TABLE 1

| Strain | SD711 | SD712 | SD713 | SD714 | SD715 | SD716 | SD717 | s | m | a | p |
|---|---|---|---|---|---|---|---|---|---|---|---|
| Morphology | rod | rod | rod | rod | rod | rod | rod | rod | rod | rod | rod |
| Gram stain | − | − | − | − | − | − | − | − | − | − | − |
| Spore | − | − | − | − | − | − | − | − | − | − | − |
| Mobility | + | + | + | + | + | + | + | + | + | + | + |
| Flagella | p.m. | p.m. | p.m. | p.m. | p.m. | p.m. | p.m. | p.m. | p.m. | p.m. | p.m. |
| Oxygen requirement | aer. | Aer. | aer. | aer. | aer. | Aer. | aer. | aer. | aer. | aer. | Aer. |
| Oxidase | + | + | + | + | + | + | + | + | + | + | + |
| Production of fluorochrome | − | − | − | − | − | − | − | − | − | − | − |
| Production of water-soluble pigment | − | − | − | − | − | − | − | − | − | − | − |
| Accumulation of PHB | + | − | − | − | − | − | − | − | − | − | − |
| Arginine dihydrolase | + | − | − | − | − | − | − | − | + | + | d |
| Growth at 41° C. | + | − | − | + | + | + | + | d | + | + | + |
| Denitrification | − | − | − | − | − | − | − | + | + | + | + |
| Liquefaction of biotin | + | − | − | − | − | − | − | − | − | d | d |
| Degradation of Tween 80 | + | + | + | + | + | + | + | + | + | d | − |
| Degradation of starch | + | + | + | − | − | − | − | + | − | − | − |
| Production of levan from sucrose | − | − | − | − | − | − | − | − | − | − | − |
| Assimilability Acetate | + | + | + | + | + | + | + | + | + | + | + |
| Glucose | + | − | − | − | − | − | − | + | + | − | − |
| Fructose | + | − | − | − | − | − | − | d | d | − | + |
| Maltose | + | − | − | − | − | − | − | + | − | − | − |
| L-Serine | + | − | − | − | − | − | − | d | + | − | d |
| L-Isoleucine | − | − | − | − | − | − | − | d | + | − | − |
| L-Aspartic acid | + | − | − | − | − | + | + | d | + | − | − |
| Propionate | + | + | + | + | + | + | + | d | + | + | + |
| Butyrate | + | + | + | + | + | + | + | + | + | d | + |
| Propylene glycol | + | + | + | + | − | + | + | + | + | d | + |
| Ethanol | + | + | + | + | + | + | + | + | + | d | + |
| Adipate | − | − | − | − | − | − | − | d | − | − | − |
| Mannitol | + | − | + | + | + | + | − | d | − | − | − |
| β-Hydroxy-butyrate | + | + | + | + | + | + | + | + | + | − | + |
| Mesaconate | + | − | − | − | − | − | − | + | + | − | + |
| Glycerate | + | + | + | + | + | + | + | d | + | − | + |
| Benzoate | + | − | − | + | + | + | + | d | d | − | − |
| Geraniol | + | − | − | − | − | − | − | − | + | − | − |
| n-Propanol | + | + | + | + | + | + | + | d | + | d | + |
| iso-Butanol | − | − | − | − | − | − | − | d | + | d | − |
| β-Alanine | + | − | − | − | − | − | − | − | + | d | d |
| L-Arginine | + | − | − | − | − | − | − | − | + | + | + |
| Ethanolamine | − | − | − | − | − | − | − | d | − | − | + |
| Betaine | + | − | − | − | − | − | − | − | + | − | + |
| Trehalose | − | − | − | − | − | − | − | − | − | − | − |
| 2-Ketogluconic acid | − | − | − | − | − | − | − | − | − | − | − |
| meso-Inositol | − | − | − | − | − | − | − | − | − | − | − |
| Quinone Type | Q-9 | Q-9 | Q-9 | Q-9 | Q-9 | Q-9 | Q-9 | Q-9 | Q-9 | Q-9 | Q-9 |
| GC content | 65% | 58% | 58% | 63% | 62% | 62% | 62% | 60.6 to 66.3% | 62.8 to 64.3% | 64 to 68% | 62 to 64% | s: Pseudomonas stutzeri; m: Pseudomonas mendocina; a: Pseudomonas alcaligenes;
p: Pseudomonas pseudoalcaligenes.
+: present or positive;
−: none or negative;
d: positive for 11 to 89% of the strains belonging to the strain concerned.
p.m. = polar monotrichous
aer. = aerobic As shown in Table 1, SD711 to SD717 strains would be considered to belong to the genus Pseudomonas since they are non-fermenting, gram negative rods having a polar flagellum and containing Q-9 quinone and more particularly these strains would be considered to be *P. stutzeri, P. mendocina*, and *P. alcaligenes, P. pseudoalcaligenes* or a closely related species in view of the fact that they have a single flagellum and produce no fluorochrome. The attributes of SD711 to SD717 strains do not completely coincide with those of *P. stutzeri, P. mendocina, P. alcaligenes*, and *P. pseudoalcaligenes*. However, based on the fact that strain SD711 have attributes relatively close to those of *P. stutzeri* and *P. mendocina* and that it is positive in starch degradation, strain SD711 was identified to be *P. stutzeri*. Strains SD712 and SD713 are positive in starch degradation and their attributes are relatively close to those of *P. stutzeri*, so these strains were identified to be *P. stutzeri*. Strains SD714 to SD717 are closest to *P. stutzeri* when compared with *P. stutzeri, P. mendocina, P. alcaligenes* and *P. pseudoalcaligenes*, but they are negative in starch degradation, so they were identified to be a species closely related to *P. stutzeri*.

DNA hybridization was used to investigate the DNA homology of strains SD714–SD717 by a photo-biotin method using microplates as described in Ezaki et al., Nihon Saikingaku Zasshi, 45, 851 (1990) and Takahashi et al., Tokyo Nogyo Daigaku Isotope Center Kenkyu Hokoku, No. 7, 69 (1993). Type strains of 5 Pseudomonas species were tested as reference. This was done The results were as follows (given as % homology between pairs of strains):

|  | SD714 | SD715 | SD716 | SD717 |
|---|---|---|---|---|
| SD714 | 100 | 86 | 85 | 83 |
| SD715 | — | 100 | 94 | 88 |
| SD716 | — | — | 100 | 89 |
| SD717 | — | — | — | 100 |
| *P. alcaligenes* IFO 14159 | 7 | 14 | 11 | 20 |
| *P. pseudoalcaligenes* IFO 14167 | 17 | 21 | 16 | 17 |
| *P. mendocina* IFO 14162 | 30 | 19 | 22 | 31 |
| *P. aeruginosa* IFO 12689 | 7 | 11 | 12 | 10 |
| *P. stutzeri* IFO 14165 | 17 | 10 | 27 | 33 |

The results show homologies above 80% among the strains SD714–SD717, and homologies of 31% or less between these strains and the five type strains. Generally, two or more strains are deemed to be the same species when they show DNA homology of at least 70%, indicating that the strains SD714–SD717 belong to the same species, different from any of the five species tested as reference. The bacteria which produce a lipase of this invention, preferably, are bacteria which show DNA homology of at least 70% with either one of SD714 to SD717 strains by DNA hybridization.

Examples of bacteria belonging to the genus Acinetobacter that produce a lipase of this invention include strain SD718 which the present inventors have isolated from soil. The bacteriological characteristics of SD718 strain were compared with *A. baumanni* and *A. haemolyticus* resembling these strains referring to the literature ((1) Bergey's Manual of Systematic Bacteriology, Vol. 1 (1984), (2) Bergey's Manual of Determinative Bacteriology, Ninth Edition (1994), and (3) P. J. M. Bouvet and P. A. D. Grimont: Int. J. Syst. Bacteriol., 36, 228 (1986)) in Table 2, below.

TABLE 2

|  |  | SD718 | *Acinetobacter baumanni* | *Acinetobacter haemolyticus* |
|---|---|---|---|---|
| (1) | Morphology | rod | rod | rod |
| (2) | Gram stain | − | − | − |
| (3) | Spore | − | − | − |
| (4) | Mobility | − | − | − |
| (5) | Oxygen requirement | aer. | aer. | aer. |
| (6) | Oxidase | − | − | − |
| (7) | Catalase | + | + | + |
| (8) | OF test | − | O | O |
| (9) | Growth at 44° C. | + | + | − |
| (10) | Growth at 41° C. | + | + | − |
| (11) | Growth at 37° C. | + | + | + |
| (12) | Liquefaction of gelatin | + | − | + |
| (13) | Haemolysis | − | − | + |
| (14) | Glutamine transferase | + | + | − |
| (15) | Utilization of citrate (Simon's medium) | + | + | + |
| (16) | Acid production from glucose | + | + | − |
| (17) | β-Xylosidase assimilability | + | + | − |
| (18) | Sodium LD-lactate | + | + | − |
| (19) | Phenyl acetate | + | + | − |
| (20) | L-Histidine | + | + | + |
| (21) | Azelaic acid | + | + | − |
| (22) | D-Malic acid | + | + | + |
| (23) | L-Leucine | + | + | + |
| (24) | L-Tyrosine | + | + | − |
| (25) | L-Ornithine | + | + | − |
| (26) | Quinone type | Q-9 | Q-9 | Q-9 |
| (27) | GC content (%) | 40 | 40–43 | 40–43 |

+ present or positive;
− none or negative;
O variable (positive for 11 to 89% of the strains belonging to the strain concerned)
aer. = aerobic From the morphological observation, physiological tests and quinone type as described above, SD718 strain was identified to be *Acinetobacter baumanni*.

SD711, SD712, SD713, SD714, SD715, SD716, SD717 and SD718 strains were deposited at National Institute of Bioscience and Human-Technology, Agency of Industrial Science and Technology, No. 1–3, Higashi 1 chome Tsukuba-shi Ibaraki-ken 305, Japan under Accession No. FERM P-15444, FERM P-15445, FERM P-15446. FERM P-15447, FERM P-15448, FERM P-15449, FERM P-154450, and FERM P-15554, respectively. The deposits were made by Showa Denko K.K., Japan, and were later assigned to Novo Nordisk A/S. The deposits were subsequently transferred to international deposits under the terms of the Budapest Treaty on Apr. 2, 1997 under the deposit numbers FERM BP-5892, FERM BP-5893, FERM BP-5894, FERM BP-5895, FERM BP-5896, FERM BP-5897, FERM BP-5898 and FERM BP-5899, respectively.

The microorganisms used for producing the a lipase of this invention include those bacteria belonging to the genus Pseudomonas such as *Pseudomonas stutzeri* and Pseudomonas sp., and those belonging to the genus Acinetobacter, such as *Acinetobacter baumanni*, and the like but not limited to particular species or genera.

Variants which produce the lipase produced by the above bacterial strains and having the characteristics mentioned below can be obtained by spontaneous mutation or artificially induced mutation. Also, microorganisms which produce a lipase of this invention can be obtained by genetic manipulation. These microorganisms can be used as lipase producing bacteria according to this invention. Conventional methods for producing variants include, for example, a method in which the original bacterial strain is subjected to artificial mutation treatment by exposure with ultraviolet rays or with a chemical such as N-methyl-N'-nitro-N-nitrosoguanidine, the thus-treated cells are spread on an agar medium containing an oil such as olive oil, the cells are screened to select those which form larger clear zones around the colonies, thereby selecting bacterial strains having excellent productivity of lipase.

Genetic manipulation methods include, for example, a method in which transformed host cells are cultivated under conditions under which the transformed cells can produce lipase, and the lipase produced is recovered from the culture broth. The transformation can be conducted, for example, by inserting the DNA sequence coding for the lipase together with suitable promoter, operator and terminator DNA sequences having the function of expressing enzymes in the host cell into a plasmid which comprises a DNA vector replicable in the host cell; or the DNA sequence coding for the lipase together with suitable promoter, operator and terminator DNA sequences having the function of realizing enzymes in the host cell can be integrated with the DNA of the host cell.

The lipase of this invention may be one produced by the technique of protein engineering whereby the DNA of the conventional lipase is modified based on the knowledge of the amino acid sequence of the lipase obtained from DNA sequence coding for the lipase.

In order to obtain DNA fragments coding for a lipase of this invention, conventional methods can be used. For example, DNA or genome library from the microorganisms of this invention can be used as an isolation source and target DNA fragments are identified using as a probe oligonucleotide synthesized based on the amino acid sequence of the lipase of this invention or of the known lipase, or clones which realize enzyme activity or clones which produce a protein that reacts with an antibody to the lipase are selected.

Method for Producing Lipase

The lipase of this invention can be obtained by cultivating a microorganism which has the ability to produce a lipase of this invention. For example, the enzymes of this invention can be obtained from culture broth of the lipase producing bacteria belonging to the genera Pseudomonas and Acinetobacter.

As nutrition sources in the culture medium, there can be used a wide variety of nutrition sources usually employed in conventional cultivation. Any carbon source can be used as far as it is selected from or contains one or more assimilable carbon compounds, for example, fats and oils, corn steep liquor, fatty acid ester surfactants, and the like. As a nitrogen source, there can be used assimilable nitrogen compounds or substances containing such compounds, for example, ammonium salts, nitrates, soybean powder, meat extract, corn steep liquor, Pharma media. As inorganic salts, there can be used phosphates, magnesium salts, and the like.

While cultivation conditions may vary more or less depending on the composition of the culture medium used, there are selected those conditions under which the target lipase of this invention can be produced. In the case of Pseudomonas cells, cultivation is conducted at a temperature in the range of 5 to 42° C., preferably 10 to 30° C., for a period of 6 to 300 hours approximately. It is desirable that the cultivation be terminated when production of the lipase has reached maximum. For the production of the lipase of this invention, the pH of the culture medium is preferably 7 to 12, and more preferably 8 to 10. In the case of Acinetobacter cells, cultivation is conducted usually at a temperature in the range of 10 to 40° C., preferably 20 to 37° C., for a period of 8 to 100 hours approximately. It is desirable that the cultivation be terminated when production of the lipase has reached maximum. For the production of the lipase of this invention, the pH of the culture medium is preferably 5 to 12, and more preferably 7 to 9. By the cultivation as described above, the target lipase can be obtained mainly as an extracellular enzyme (occurring in the culture medium).

Separation and Purification of Lipase

The lipase of this invention can be recovered from the culture broth by conventional isolation and purification methods for recovery of lipase.

More particularly, in a first step, cells and solid contents of the culture broth are separated from the culture broth by a suitable known method such as a filtration method or a centrifugation method to collect supernatant or filtrate, the liquid thus obtained is used in the next step after it is concentrated or without concentration. In a second step, there are used separation or purification methods such as salting out method in which a soluble salt is added to precipitate enzyme, organic solvent precipitation methods in which hydrophilic organic solvents are added to precipitate enzyme or contaminants, adsorption and desorption methods using ion exchange resin, gel filtration methods, spraying methods with or without stabilization aids, freezing and thawing methods, and the like singly or in combination. Thus, the lipase of this invention can be obtained.

Assay for Lipase Activity

The measurement of lipase activity (titer) is conducted by an assay method using as a substrate an olive oil/polyvinyl alcohol emulsion, more specifically, as described below.

The olive oil/polyvinyl alcohol emulsion is a homogenate prepared by adding 10 g of olive oil to 100 g of an aqueous 2% polyvinyl alcohol solution (POVAL PVA 117:POVAL PVA205=9:1, trade names for products by KURARAY CO., LTD.) and homogenizing the resulting mixture at a speed of 30,000 rpm for 10 minutes while ice cooling. A mixture of 3 ml of the emulsion, 30 ml of a 36.7 mM sodium chloride/ 13.8 mM calcium chloride solution, 0.1 ml of an enzyme solution is allowed to stand at 30° C. for reaction, and the reaction mixture is kept at pH 9 by a pH stat titration method with an aqueous 200 mM sodium hydroxide solution. 1 unit (1U) is the amount of enzyme which gives a titration rate of 1 $\mu$mol per minute of sodium hydroxide.

Properties of Lipase in Detergent Solution

The lipase of this invention shows excellent washing effect not observed in the known lipases. More specifically, the lipase of this invention satisfies at least one, preferably 2 or more, or 3 or more, and more preferably all, of the conditions 1) to 4) below. Preferably, it also satisfies the condition 5) below.

Low Temperature Characteristics

The optimum temperature is at least 40° C. and the activity at 1° C. is at least 20%, preferably at least 30%, of the activity at 30° C.

Activity in the Presence of a Bleaching Agent

The decomposition rate of p-nitrophenyl palmitate in a solution containing 0.046% LAS at 25° C. in the presence of 0.5% hydrogen peroxide is at least 80% of the decomposition rate in the absence of hydrogen peroxide.

When measured in a solution of Synthetic Detergent (1), (3) (each composition is described in Example 5 below) or Tide With Bleach (a trade name for a product by P&G) containing 0.5% of hydrogen peroxide by the method described in Example 6 below, the lipase has an activity which is at least 80% of the activity when measured without addition of hydrogen peroxide (the case where Synthetic Detergent (1) is used corresponds to 0.046% LAS). SDL712 to SDL717 are examples of lipases with this property.

Stability in the Presence of a Bleaching Agent

When held in a solution containing 0.05% LAS and 0.55% hydrogen peroxide at 25° C. for 1 hour, the lipase has a residual activity which is at least 50%, preferably at least 60%, and more preferably at least 70%, of the initial activity.

The lipase has a stability which is at least 50% when measured by the method described in Example 7 below in a solution of Synthetic Detergent (1), (2) or Tide With Bleach (a trade name for a product by P&G) containing 0.55% of hydrogen peroxide (the case where Synthetic Detergent (1) is used corresponds to 0.05% LAS). SDL711 and SDL714 to SDL717 are examples of lipases with this property.

Activity in the Presence of a High Concentration of LAS

The decomposition rate of p-nitrophenyl palmitate in a solution at 25° C. containing 0.2% LAS is at least 50% of the decomposition rate in a solution containing 0.02% LAS.

When measured by the method described in Example 8 below, the degradation rate of p-nitrophenyl palmitate in a solution at 25° C. containing 0.2% LAS is at least 50% of the degradation rate of p-nitrophenyl paimitate in a solution containing 0.02% LAS. SDL714 to SDL717 are examples of lipases with this property.

Difference in Activity with or without LAS

The activity measured in a solution containing 0.02% of LAS using an olive oil emulsion as a substrate is at least 20% of the activity measured without addition of LAS.

When measured by the method described in Example 5 below, the lipase shows an activity of at least 20% in detergent solutions of Synthetic Detergents (1) to (3), Tide With Bleach (a trade name for a product by P&G), ULTRA ARIEL (a trade name for a product by P&G), NEW COMPACT ATTACK (a trade name for a product by KAO CORPORATION, hereafter abbreviated as "ATTACK"), or CONCENTRATED ENZYME TOP (a trade name for a product of LION CO., LTD., hereafter abbreviated as "TOP").

The detergent solutions used contained anion andlor non-ionic surfactants in final amounts of 0.02 to 0.04% (the case where Synthetic Detergent (2) is used corresponds to 0.02% LAS).

Other Lipase Properties

Description is made of properties of the lipase of this invention with reference to the lipases produced by SD711 to SD718 strains (hereafter, each lipase is named by replacing SD in the name of the strain producing the lipase by SDL). Action The lipase acts on higher fatty acid esters such as triglyceride to hydrolyze the esters.

Substrate Specificity

The lipase hydrolyzes a wide variety of glycerides, esters and the like.

Action pH and Optimum pH

The action pH and optimum pH are measured by a titration method using the above-described emulsion as a substrate. In this case, the reaction is performed at various pH values within the range of pH 8.0 to 12.0. FIGS. 1 to 8 illustrate the relationship between the reaction pH of the relative activity. When measured at pH within the range of 8.0 to 12.0, each lipase is active throughout the range from pH 8.0 to 12.0 and has an optimum pH within the range of pH 8.5 to 12. The approximate pH optimum of each lipase is as follows. Errors are within about ±0.5.

| Lipase | pH optimum |
| --- | --- |
| SDL711 | 9 to 10.5 |
| SDL712 | 9.5 to 11 |
| SDL713 | 9.5 to 11 |
| SDL714 | 11.5 |
| SDL715 | 11.5 |
| SDL716 | 10 to 11 |
| SDL717 | 11 |
| SDL718 | 10 to 10.5 |

Action Temperature and Optimum Temperature

Action temperature and optimum temperature are measured by a titration method using the above-described emulsion as a substrate. Reaction temperatures are measured at various temperatures within the range of 1 to 65° C. FIGS. 9 to 16 and Table 3 illustrate the relationship between the reaction temperature and relative activity.

When measured within a range of 1 to 65° C., each enzyme is active throughout the range from 1 to 65° C. Table 3, below, shows the relative activity at 1° C. taking the activity at 30° C. as 100%), the temperature coefficient of the activity in % per ° C., and the optimum temperature. Results for LIPOMAX® (trade name for a roduct by Gist-Brocades) are shown for comparison.

TABLE 3

Relationship between enzyme activity and temperature

| Lipase | Relative activity at 1° C. (%) | Temperature Coefficient (%/° C.) | Optimum temperature |
| --- | --- | --- | --- |
| SDL711 | 14 | 7.0 | 60° C. |
| SDL712 | 22 | 5.4 | 55° C. |
| SDL713 | 23 | 5.2 | 55° C. |
| SDL714 | 36 | 3.6 | 54° C. |
| SDL715 | 31 | 4.1 | 50° C. |
| SDL716 | 38 | 3.4 | 52° C. |
| SDL717 | 35 | 3.7 | 51° C. |
| SDL718 | 40 | 3.2 | 46° C. |
| LIPOMAX | 11 | 8.0 | |

The optimum temperature of each enzyme is in the range of 45 to 65° C. Errors are within about ±3° C. Lipases SDL712 to SDL718 had an activity at 1° C. of at least 20% of the activity at 30° C., particularly at least 30% in the case of SDL714 to SDL718.

Temperature Stability

The residual activity after incubation for 30 minutes at pH 9 at various temperatures is measured by a titration method using the above-described emulsion as a substrate. Each enzyme shows a residual activity of at least 90% after incubation at 30° C. and at least 50% after incubation at 50° C.

Temperature Coefficient of Activity

As shown in Table 2, lipases SDL712 to SDL718 show a temperature coefficient of activity of not higher than 5.5%/° C. in contrast, the known enzyme LIPOMAX (trade name for a product by Gist-Brocades) shows a temperature coefficient of activity of 8.0%/° C.

pH Stability

Residual activities after incubation treatment for 30 minutes at 30° C. at various pH are measured by a titration method using the above-described emulsion as a substrate. Each enzyme shows a residual activity of at least 50% after the treatment at pH 5 to 10.

Molecular Weight

The lipases have a molecular weight within the range of 30,000±3,500 as measured by SDS-polyacrylamide gel electrophoresis. The mo lecul ar weight of each lipase is as follows:

| Lipase | Molecular weight |
| --- | --- |
| SDL711 | 30,500 ± 3,000 |
| SDL712 | 30,000 ± 3,000 |
| SDL713 | 30,000 ± 3,000 |
| SDL714 | 29,500 ± 3,000 |
| SDL715 | 29,500 ± 3,000 |
| SDL716 | 30,000 ± 3,000 |
| SDL717 | 30,000 ± 3,000 |
| SDL718 | 30,500 ± 3,000 |

Isoelectric Point

The isoelectric points of lipases SDL711to SDL718 measured by isoelectric point electrophoresis are within the range of 6.0±2.0.

Application of Lipolytic Enzyme

The lipolytic enzyme of the invention may be used in conventional applications of lipolytic enzyme, particularly at a high pH, e.g. in laundry and dishwash detergents, in institutional and industrial cleaning and in leather processing.

The lipolytic enzymes of the invention can also be used for interesterification, for total hydrolysis of fats and oils and in optical isomer resolution processes.

Detergent Additive

According to the invention, the lipolytic enzyme may typically be used as an additive in a detergent composition. This additive is conveniently formulated as a non-dusting granulate, a stabilized liquid, a slurry or a protected enzyme. The detergent additive may conveniently contain the lipolytic enzyme of this in vention in an amount of 0.01–100 mg pure enzyme protein per g of the additive.

Non-dusting granulates may be produced, e.g., as disclosed in U.S. Pat. No. 4,106,991 and 4,661,452 (both to Novo Industri A/S) and may optional ly be coated by methods known in the art. Examples of waxy coating materials are poly(ethylene oxide) products (polyethylene glycol, PEG) with mean molecular weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in patent GB 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in EP 238,216.

Detergent Composition

Detergent compositions comprising a lipase with the above-described properties are provided by this invention. There is no limitation on the amount of lipase to be blended in the detergent compositions of this invention. However, generally, the lipase can be blended in amounts of 50 to 50,000 units, preferably 100 to 10,000 units, per gram of the detergent composition. If the amount of lipase is too small, no sufficient improvement of washing effect can be obtained, and with an excess amount of the lipase, an increase in washing effect is small for the amount of the lipase blended, which is undesirable from economical viewpoint.

Representative formulations of the detergent composition of this invention include a detergent composition which contains 10 to 50% by weight of a surfactant, 0 to 50% by weight of a builder, 1 to 50% by weight of an alkali agent or inorganic electrolyte, and 0.1 to 5% by weight of at least one blending component selected from the group consisting of an anti-redeposition agent, an enzyme, a bleaching agent, a fluorescent dye, a caking inhibitor, and an antioxidant.

The surfactant can be any conventionally used surfactant usually blended in detergent compositions. The detergent cvomposition will usually contain an anionic surfactant, singly or together with other surfactants; advantageously, the iipases of the invention are effective in such detergents. Examples of surfactants are soaps, aliphatic sulfates such as straight or branched chain alkyl or alkenyl sulfates, amide sulfates, alkyl or alkenyl ether sulfates which have a straight or branched chain alkyl or alkenyl group and to which one or more of ethylene oxide, propylene oxide and butylene oxide are added; aliphatic sulfonates such as alkylsulfonates, amidosulfonates, dialkyl sulfosuccinates, sulfonates of a-olefins, vinylidene type olefins and internal olefins; aromatic sulfonates such as straight or branched chain alkylbenzene sulfonates; alkyl or alkenyl ether carboxylates or carboxamides which have a straight or branched chain alkyl or alkenyl group and to which one or more of ethylene oxide, propylene oxide and butylene oxide are added; alpha-sulfoaliphatic acid salts or esters; amino acid surfactants; phosphate surfactants such as alkyl or alkenyl hydrogen phosphate esters, alkyl or alkenyl phosphates; sulfonic acid type amphoteric surfactant; betaine type amphoteric surfactants, aromatic sulfonates such as straight or branched chain alkylbenzene sulfonates; polyoxyethylene alkyl phenyl ether which have a straight or branched chain alkyl or alkenyl group and to which one or more of ethylene oxide, propylene oxide and butylene oxide are added; higher fatty acid alkanolamides or alkylene oxide adducts thereof; sucrose fatty acid esters, fatty acid glyceride monoesters; alkyl or alkenyl amine oxides; tetraalkylammonium salt type cationic surfactants; and the like. In the case of anionic surfactants, the cation is preferably sodium ion or potassium ion. These surfactants can be used singly or two or more of them can be used in combinations.

The detergent may contain a builder, alkali agent and/or inorganic electrolyte. Examples are alkali metal salts, phosphates such as orthophosphates, pyrophosphates, tripolyphosphates, metaphosphates, hexametaphosphates, and phytates; phosphonates such as ethane-1,1-diphosphonic acid and its derivatives, ethanehydroxy-1,1,2-triphosphonic acid, ethane-1,2-dicarboxy-1,2-diphosphonic acid, and methanehydroxyphosphonic aid; phosphonocarboxylate such as 2-phosphonobutane-1,2-dicarboxylate, 1-phosphonobutane-2,3,4-tricarboxylate, and a-methylphosphonosuccinate; amino acid salts such as aspartate and glutamate; aminopolyacetate such as nitrilotriacetate, ethylenediaminetetraacetate, and diethylenetriaminepentaacetate; polymeric electrolytes such as polyacrylic acid, polyitaconic acid, polymaleic acid, maleic anhydride copolymers, and carboxymethylcellulose salts;

nondissociable polymers such as polyethylene glycol and polyvinyl alcohols; carboxymethylate of diglycolic acid, oxydisuccinic acid, carboxymethyloxysuccinic acid, gluconic acid, citric acid, lactic acid, tartaric acid, sucrose, and lactose; carboxymethylate of pentaerythritol and the like; organic acid salts such as benzenepolycarboxylate, oxalates, malate, oxydisuccinate, and gluconate; aluminosilicate such as zeolite; inorganic salts such as carbonates, sesquicarbonate, sulfates and metasilicate. Also, there can be used organic substances such as starch and urea and inorganic compounds such as sodium chloride and bentonite. Further, as the organic alkali agent, there can be used triethanolamine, diethanolamine, monoethanolamine, triisopropanolamine and the like.

As described above, the detergent composition of this invention will typically contain a surfactant, a lipase, and an alkali agent or inorganic electrolyte. It may contain, if desired, amphoteric surfactants, bleaching agents (described further below), pigments, builders, recontamination inhibitors, for example, polyethylene glycol, polyvinyl alcohol, polyvinylpyrrolidone, and carboxymethylcellulose, caking inhibitors, antioxidants, other enzymes such as proteases.

The detergent composition of the invention may be in any convenient form, e.g. as powder, granules, paste or liquid. A liquid detergent may be aqueous, typically containing up to 70% water and 0–30% organic solvent, or non-aqueous.

Bleaching Agent

Advantageously, the invention provides lipases with good washing effect in detergents containing a bleaching agent. The bleaching agent can include one or more oxygen bleaching agents of the peroxy type and, depending upon the bleaching agent chosen, one or more bleach activators. When present, oxygen bleaching compounds will typically be present at levels of from about 1% to about 25%. Oxygen bleaching agents are particularly useful in granular detergents.

The oxygen bleach may be a salt (e.g. an alkali metal salt, particularly a sodium salt) of an inorganic peroxy acid, e.g. a perborate (e.g. PB1 or PB4), percarbonate or persulfate. Another category of oxygen bleaching agents encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. Pat. No. 740,446, EP 0 133 354 and U.S. Pat. No. 4,412,934. Highly preferred bleaching agents also include 6-nonylamino-6-oxoperoxycaproic acid as described in U.S. Pat. No. 4,634,551.

The oxygen bleach may be a precursor of hydrogen peroxide and may be used in combination with bleach activators such as tetra-acetylethylenediamine (TAED), nonanoyloxybenzenesulfonate (NOBS, described in U.S. Pat. No. 4,412,934), 3,5-trimethyl-hexsanoloxybenzenesulfonate (ISONOBS, described in EP 120 591) or pentaacetylglucose (PAG), which are perhydrolyzed to form a peracid as the active bleaching species, leading to improved bleaching effect. In addition, very suitable are the bleach activators C8(6-octanamido-caproyl) oxybenzene-sulfonate, C9(6-nonanamido caproyl) oxybenzenesulfonate and C10 (6-decanamido caproyl) oxybenzenesulfonate or mixtures thereof. Also suitable activators are acylated citrate esters such as disclosed in European Patent Application No. 91870207.7.

The hydrogen peroxide may also be present by adding an enzymatic system (i.e. an enzyme and a substrate therefore) which is capable of generation of hydrogen peroxide at the beginning or during the washing and/or rinsing process. Such enzymatic systems are disclosed in European Patent Application EP 0 537 381.

Bleaching agents other than oxygen bleaching agents are also known in the art and can be utilized herein. One type of non-oxygen bleaching agent of particular interest includes photoactivated bleaching agents such as the sulfonated zinc andlor aluminium phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent composition will contain about 0.025% to about 1.25%, by weight, of sulfonated zinc phthalocyanine.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

Bleaching agents may also comprise a manganese catalyst. The manganese catalyst may, e.g., be one of the compounds described in "Efficient manganese catalysts for low-temperature bleaching", Nature 369, 1994, pp. 637–639.

EXAMPLES

Next, this invention will be described by examples. However, this invention should not be construed as being limited thereto. In the following description, all percentages (%) are by weight unless otherwise indicated specifically.

Example 1

Cultivation of Bacterial Strains SD711 to SD717

A liquid medium (2 ml) containing 0.5% of Tween 80, 0.1% of ammonium nitrate, 1% of dipotassium hydrogen phosphate, 0.4% of potassium dihydrogen phosphate, 0.05% of calcium chloride dihydrate, 0.3% of magnesium sulfate heptahydrate, 0.004% of ferric chloride hexahydrate, 0.0003% of manganese tetra- or pentahydrate, and 0.5% of sodium carbonate was charged in a test tube of 18 mm in diameter, and autoclaved at 121° C. for 20 minutes. Thereafter, a loopful of one of the strains SD711 to SD717 was inoculated in the liquid culture and incubated at 25° C. for 20 hours with shaking at 300 rpm. After the incubation, the cells were removed by centrifugation to obtain a lipase solution. The solutions had a lipase activity of about 8 U/ml for strain SD711, about 0.2 U/ml for SD712 and SD713, and about 0.1 U/ml for SD714 to SD717.

Example 2

Cultivation of Strains SD711to SD717 and Recovery of Lipase

A liquid medium (2 liters) having the same composition as described in Example 1 was charged in a 5-liter incubation tank and autoclaved at 121° C. for 20 minutes. Thereafter, one of strains SD711 to SD717 was inoculated in the liquid culture and incubated at 25° C. for 40 hours with aeration and shaking at 1,000 rpm. After the incubation, the cells were removed by centrifugation to obtain a lipase solution. The solutions had a lipase activity of about 20 U/ml for SD711 strain, about 1 U/ml for SD712 and SD713 strains, and about 0.5 U/ml for SD714 to SD717 strains.

The lipase solution of SD711 thus obtained was treated by salting-out with ammonium sulfate and collecting precipitate from fractions at 20 to 50% saturation. The precipitate was desalted and lyophilized to obtain a crude lipase powder.

The lipase solutions from strains SD712 and SD713 were concentrated and treated by salting-out with ammonium sulfate and collecting precipitate from fractions at 20 to 50% saturation. The precipitates were desalted and lyophilized to obtain crude lipase powders.

The tipase solutions from strains SD714 to SD717 were concentrated, desalted and precipitated by an acetone precipitation method to obtain precipitation in 20 to 50% acetone fractions. The precipitates were dried in vacuo to obtain crude lipase powders.

Example 3

Cultivation of Strain SD718 and Recovery of Lipase

A liquid medium (2 liters) containing 2% of Tween 80, 0.4% of ammonium sulfate, 1% of dipotassium hydrogen phosphate, 0.4% of potassium dihydrogen phosphate, 0.05% of calcium chloride dihydrate, 0.3% of magnesium sulfate heptahydrate, 0.03% of ferric sulfate heptahydrate, 0.005% of manganese tetra- or pentahydrate, and 0.1% of sodium carbonate was charged in a 5-liter incubation tank, and autoclaved at 121° C. for 20 minutes. Thereafter, *Acinetobacter baumanni* strain SD718 was inoculated in the liquid culture and incubated at 30° C. for 24 hours with aeration and shaking at 1,000 rpm. After the incubation, the cells were removed by centrifugation to obtain a lipase solution. The solution had a lipase activity of about 500 U/ml. The lipase solution was treated by salting-out with ammonium sulfate and collecting precipitate from the fractions at 20 to 30% saturation. The precipitate was desaited and lyophilized to obtain a crude lipase powder.

Example 4

Purification of Lipases

The crude lipase powder obtained in Example 2 or 3 was dissolved in 10 mM Tris-hydrochloride buffer solution (pH 8) containing 3% of Triton X-100 and sequentially subjected to ion exchange chromatography with DEAE-Cellulofine A-500 (a trade name for a product by SEIKAGAKU CO., LTD.), hydrophobic chromatography with Butyl-Toyopearl 650M (a trade name for a product by TOSOH CORPORATION), ion exchange chromatography with DEAE-Cellulofine A-500 (a trade name for a product by SEIKAGAKU CO., LTD.), and reversed phase partition chromatography with Shodex RSpak RP18-415 (a trade name for a product by SHOWA DENKO K.K.) to obtain a purified enzyme. The purified products thus obtained were confirmed to be homogeneous by SDS polyacrylamide gel electrophoresis.

Example 5

Activity in Detergent Solutions

The lipases obtained in Example 2 were used for measurement of their activity in detergent solutions. The results were compared with those obtained with a commercially available lipase derived from Chromobacter viscosum and LIPOMAX (trade name for a detergent lipase from GIST-BROCADES).

The activity of the enzymes in the detergent solutions were measured in the same manner as in the above-described titration method, except that detergent solutions were used instead of the salt solutions and the reaction was conducted at 35° C. at pH 10.

The detergents used were Synthetic Detergents (1) to (3), commercially available detergents, i.e., TIDE WITH BLEACH (a trade name for a product by P&G), ULTRA ARIEL (a trade name for a product by P&G), NEW COMPACT ATTACK (a trade name for a product by KAO CORPORATION, hereafter abbreviated as "ATTACK"), or CONCENTRATED ENZYME TOP (a trade name for a product of LION CO., LTD., hereafter abbreviated as "TOP"). The concentrations and compositions of the detergent solutions are shown below. These detergents were dissolved in aqueous 0.54 mM calcium chloride solutions.

Synthetic Detergent (1) (26% of LAS, and 74% of detergent base): 0.169%

Synthetic Detergent (2) (15% of LAS, and 85% of detergent base): 0.147%

Synthetic Detergent (3) (19% of LAS, 7% of POEAE, and 74% of detergent base): 0.169%

TIDE WITH BLEACH (anionic surfactant, bleaching agent and an enzyme were contained): 0.159%

ULTRA ARIEL (35% of anionic/nonionic surfactant, a bleaching agent, and an nzyme were contained): 0.11%

ATTACK (39% of anionic/nonionic surfactant and an enzyme were contained): 0.073%

TOP (39% anionic surfactant and an enzyme were contained): 0.073%.

Here, "POEAE" and the detergent base are as follows:

Detergent base: 20% of zeolite, 69.4% of sodium sulfate, 3.5% of sodium carbonate, 5.9% of sodium silicate, and 1.2% of carboxymethyicellulose.

POEAE: polyoxyethylene alkyl ether

Table 4 shows the relative activities of the lipase taking the activity without addition of the detergent as 100.

TABLE 4

| | | Relative Activity of Lipases in Detergent Solutions | | | | | | |
|---|---|---|---|---|---|---|---|---|
| Lipase added | No Detergent | Synthetic detergent (1) | Synthetic detergent (2) | Synthetic detergent (3) | TIDE WITH BLEACH | ULTRA ARIEL | ATTACK | TOP |
| SDL711 | 100 | 35 | 42 | 70 | 76 | 41 | 38 | 37 |
| SDL712 | 100 | 21 | 44 | 116 | 148 | 72 | 46 | 87 |

TABLE 4-continued

Relative Activity of Lipases in Detergent Solutions

| Lipase added | No Detergent | Synthetic detergent (1) | Synthetic detergent (2) | Synthetic detergent (3) | TIDE WITH BLEACH | ULTRA ARIEL | ATTACK | TOP |
|---|---|---|---|---|---|---|---|---|
| SDL713 | 100 | 20 | 48 | 119 | 151 | 84 | 52 | 86 |
| SDL714 | 100 | 133 | 124 | 87 | 128 | 108 | 76 | 117 |
| SDL715 | 100 | 121 | 73 | 85 | 101 | 70 | 43 | 62 |
| SDL716 | 100 | 114 | 112 | 81 | 90 | 51 | 37 | 41 |
| SDL717 | 100 | 76 | 122 | 72 | 123 | 77 | 65 | 83 |
| SDL718 | 100 | 20 | 25 | 64 | 22 | 26 | 73 | 51 |
| C. visc. | 100 | 1 | 1 | 3 | 2 | 2 | 3 | 1 |
| LMX | 100 | 17 | 60 | 54 | 83 | 19 | 18 | 29 |

SDL711 to SDL718 were lipases obtained from strains SD711 to SD718.
C. visc. indicates a lipase derived from *Chromobacter viscosum*, and LMX is LIPOMAX.

Example 6

Influence of Bleaching Agent on Activity

The lipases obtained in Example 2 were tested for activity in a bleaching agent solution and the results obtained were compared with the same lipase as in Example 5. Table 5 shows the results obtained. The lipase derived from *Chromobacter viscosum* was excluded from this example since it showed little activity in detergent solutions. The activities were measured by mixing 0.1 ml of an enzyme solution, 2.5 ml of a detergent solution, and 0.25 ml of a 0.2% p-nitrophenyl palmitate solution in 2-propanol, reacting the mixture at 25° C., and measuring a rate of increase in optical density (A405) generated by decomposition of p-nitrophenyi palmitate due to the enzymatic reaction. The detergent solutions used were prepared by dissolving the detergents, i.e., Synthetic Detergents (1) and (3) and TIDE WITH BLEACH, so that the resulting solution contained 2,000 ppm of the detergent, 0.27 mM of calcium chloride, and 10 mM of CHES (2-(Cyclohexylamino)ethanesulfonic acid), and 0.57% of hydrogen peroxide, and adjusted to pH 9.3. In the case of Synthetic Detergents (1) and (3), the lipase activity is expressed as relative activity, taking the activity measured in a solution without hydrogen peroxide as 100. In the case of TIDE WITH BLEACH, the lipase activity is expressed as relative activity taking as 100 the activity measured in a detergent solution without hydrogen peroxide after decomposing the bleaching agent.

TABLE 5

Influence of Bleaching Agent on Activity (unit: %)

| Lipase added | Synthetic detergent (1) | Synthetic detergent (3) | TIDE WITH BLEACH |
|---|---|---|---|
| SD711 | 51 | 61 | 62 |
| SD712 | 85 | 165 | 82 |
| SD713 | 87 | 157 | 88 |
| SD714 | 123 | 138 | 136 |
| SD715 | 114 | 132 | 126 |
| SD716 | 100 | 104 | 109 |
| SD717 | 89 | 87 | 95 |
| LMX | 43 | 39 | 71 |

Example 7

Stability in Detergent Solutions Containing a Bleaching Agent

The lipases obtained in Example 2 were tested for stability in detergent solutions containing a bleaching agent, and the results were compared with the same lipase as in Example 6. Table 6 shows the results obtained. The stability was determined by mixing 0.1 ml of an enzyme solution and 2.5 ml of a detergent solution and measuring the activity immediately after the mixing and after incubation at 25° C. for 1 hour. The stability was calculated according to the formula below:

Stability=(Activity 1 Hour After the Mixing)/(Activity Immediately After the Mixing)

As the detergent solutions were used those containing hydrogen peroxide as employed in Example 6.

TABLE 6

Stability in Detergent Solutions Containing a Bleaching Agent

| Lipase added | Synthetic detergent (1) | Synthetic detergent (3) | TIDE WITH BLEACH |
|---|---|---|---|
| SD711 | 61 | 85 | 72 |
| SD712 | 11 | 18 | 19 |
| SD713 | 12 | 17 | 21 |
| SD714 | 96 | 98 | 91 |
| SD715 | 93 | 94 | 95 |
| SD716 | 87 | 84 | 81 |
| SD717 | 90 | 89 | 93 |
| LMX | 29 | 32 | 43 |

Example 8

Activity at High Concentration of Anionic Surfactant

The lipases obtained in Example 2 were tested for activity in a solution with a high concentration of anionic surfactant and the results obtained were compared with the same lipase as in Example 5. Table 7 shows the results obtained. The lipase derived from Chromobacter viscosum was excluded from this example since it showed little activity in detergent solutions. The activity was measured by mixing 0.1 ml of an enzyme solution, 2.5 ml of a detergent solution, and 0.25 ml of a 0.2% p-nitrophenyl palmitate solution in 2-propanol, reacting the mixture at 25° C., and measuring the rate of increase in optical density (A405) generated by decomposition of p-nitrophenyl palmitate due to the enzymatic reaction. The detergent solutions used were prepared by dissolving the detergents, i.e., Synthetic Detergents (1) and (2) in an aqueous solution containing 0.27 mM calcium chloride and 10 mM CHES, so that the resulting solution contained 0.87% of Synthetic Detergent (1) or 0.15% of Synthetic Detergent (2), adjusted to pH 9.3. The results are expressed as relative activity in Synthetic Detergent (1) taking the activity measured with the detergent solution containing Synthetic Detergent (2) as 100.

TABLE 7

Relative Activity (unit: %) of Lipase in High Concentration Anionic Detergent Solutions

| Lipase Added | Relative Activity |
| --- | --- |
| SD711 | 23 |
| SD712 | 8 |
| SD713 | 10 |
| SD714 | 61 |
| SD715 | 59 |
| SD716 | 52 |
| SD717 | 54 |
| LMX | 7 |

Example 9

Evaluation of Washing Effect

Washing tests were conducted to evaluate the washing effect of the lipases obtained in Examples 2 and 3, and a commercially available lipase derived from Chromobacter viscosum, together with TIDE WITH BLEACH, a commercial bleach-containing detergent, ULTRA ARIEL, ATTACK, TOP, and Synthetic Detergent (1). Table 8 shows the results obtained. The washing effects were evaluated as follows.

The water used in this example was deionized water to which 20 ppm of calcium ions were added. In the water was dissolved a commercially available detergent at the standard use concentration or Synthetic Detergent (1) at a concentration of 1.5 g/liter. The lipase was added to the resulting detergent solution in an amount of 1U/ml. As soiled cloth were used pieces of degreased cotton cloth painted with a lipstick at a density of 10 mg/cm$^2$ and dried at 75° C. for 30 minutes and then left to stand at room temperature for one night. The washing machine used was Terg-O-Tometer. Three pieces of the dirt cloth each having a size of 12 cm×12 cm were washed with 1 liter of the detergent solution at 25° C. for 20 minutes with stirring at 80 rpm. After the washing, the pieces of the cloth were rinsed with 1 liter of water at 25° C. twice each time for 3 minutes, followed by drying at room temperature. The enzymatic effect was evaluated in terms of ΔΔZ, i.e., difference in ΔZ with and without addition of an enzyme (=ΔZ value obtained with addition of an enzyme– ΔZ value without addition of the enzyme). Further, ATTACK, which gave a relatively low enzymatic effect, was used for evaluation by soaking. Soaking was performed by introducing pieces of soiled cloth into 167 ml of a detergent solution having a concentration by 6 times as high as the standard use concentration in Terg-O-Tometer, keeping the temperature at 25° C., diluting the solution to 6 folds after 1 hour, and thereafter conducting washing in the same manner as the other detergents.

Here, ΔZ is the difference in Z values of soiled cloth before and after the washing (=Z value after the washing–Z value before the washing). The Z values are Z values defined in CIE color specification system and measured using a color difference meter.

The standard use concentration were as follows:

TIDE WITH BLEACH (P&G): 0.14%
ULTRA ARIEL (P&G): 0.10%
ATTACK (KAO): 0.067%
TOP (LION): 0.067%

TABLE 8

Evaluation of Cleaning Effect (25° C. ΔΔZ values)

| Lipase added | Synthetic Detergent (1) | TIDE WITH BLEACH | ULTRA ARIEL | AT-TACK | TOP | ATTACK (DIPPING) |
| --- | --- | --- | --- | --- | --- | --- |
| None | 0 | 0 | 0 | 0 | 0 | 0 |
| SDL711 | 0.4 | 2.0 | 1.5 | 1.6 | 1.4 | 2.2 |
| SDL712 | 0.3 | 0.8 | 1.6 | 1.2 | 2.0 | 1.5 |
| SDL713 | 0.4 | 0.9 | 1.4 | 1.4 | 2.1 | 1.6 |
| SDL714 | 6.2 | 3.6 | 2.6 | 2.4 | 2.6 | 7.2 |
| SDL715 | 6.5 | 3.4 | 2.8 | 2.3 | 2.9 | 7.0 |
| SDL716 | 5.5 | 4.4 | 1.5 | 0.9 | 1.7 | 3.3 |
| SDL717 | 2.7 | 4.1 | 2.2 | 1.6 | 1.8 | 4.4 |
| SDL718 | 0.1 | 0.1 | 0.3 | 0.8 | 0.9 | 1.0 |
| C. visc. | <0.1 | <0.1 | <0.1 | <0.1 | <0.1 | <0.1 |
| LMX | 0.4 | 0.8 | 0.4 | 0.2 | 1.0 | 0.2 |

In washing with the lipase of this invention or the detergent compositions of this invention, the washing effect of the lipase in the detergent solutions is higher than that of the comparative detergent compositions containing no lipase. Comparing the results obtained in Examples 5 to 7, it can be seen that use of lipase which has a rate of decomposition of p-nitrophenyl palmitate higher in detergent solutions containing 0.5% of hydrogen peroxide than in detergent solutions containing no hydrogen peroxide or which is stable in detergent solutions containing 0.55% of hydrogen peroxide gives a high washing effect in detergent solutions. It can also be seen from comparison with the results obtained in Example 8 that enzyme having high activity in detergent solutions containing surfactants in high concentrations exhibit excellent washing effect in dipping washing.

Example 10

Evaluation of Washing Effect at 5° C.

Washing tests were conducted in the same manner as in Example 9, except that the washing temperature was set to 5° C. The lipase derived from *Chromobacter viscosum* was excluded from this example since it showed little activity in detergent solutions. Table 9 shows the results obtained.

TABLE 9

Evaluation of Cleaning Effect (5° C., ΔZ values)

| Lipase added | Synthetic Detergent (1) | TIDE WITH BLEACH | ULTRA ARIEL | ATTACK | TOP |
| --- | --- | --- | --- | --- | --- |
| None | 0 | 0 | 0 | 0 | 0 |
| SDL711 | 0.1 | 0.4 | 0.4 | 0.3 | 0.3 |
| SDL712 | 0.2 | 0.4 | 0.7 | 0.6 | 1.0 |
| SDL713 | 0.2 | 0.5 | 0.6 | 0.6 | 0.9 |
| SDL714 | 3.0 | 1.8 | 1.2 | 1.2 | 1.4 |
| SDL715 | 3.1 | 1.6 | 1.4 | 1.0 | 1.4 |
| SDL716 | 2.8 | 2.3 | 0.8 | 0.6 | 0.8 |
| SDL717 | 1.5 | 2.1 | 1.0 | 0.7 | 0.9 |
| SDL718 | 0.1 | 0.4 | 0.5 | 0.7 | 0.8 |
| LMX | <0.1 | 0.1 | <0.1 | <0.1 | 0.2 |

In washing at 5° C., use of LIPOMAX (LMX) showed substantially no activity whereas use of SDL711 to SDL718 resulted in effective activity. SDL712 to SDL718, which have small temperature coefficients of activity, in particular SDL714 to SDL718, showed a less decrease in ΔΔZ value as compared with washing at 25° C.

From the results obtained in Examples 5 to 10 above, it can be seen that the enzymes of this invention are lipases having high activity in detergent solutions and less vulnerable to influences of the presence of bleaching agents in the detergent solutions so that they show high washing effect in detergent solutions. Further, it can be seen that the enzymes of this invention having low temperature coefficients of activity are advantageous in washing at low temperatures.

Example 11

Evaluation of First-Wash Effect

Lipase SDL714 was evaluated in washing tests and compared with two commercial lipolytic enzymes from Pseudomonas were included as reference: Lumafast (*P. mendocina*) and Lipomax (*P. pseudoalcaligenes*). The washing tests were made at the following conditions:

| Equipment | Tergotometer |
|---|---|
| Swatches | 7 stained cotton swatches (9 × 9 cm) per beaker |
| Stain | Lard colored with sudan red (0.75 mg sudan red/g of lard, 50 μl of lard/swatch |
| Detergent | Commercial detergent Ariel Future with bleach, heated to inactivate the enzymes, 5 g/l |
| Volume | 1000 ml wash liquor per beaker |
| Wash temperature | 30° C. |
| Wash time | 20 minutes |
| Rinsing | 15 minutes in running tap water |
| Drying | Overnight at room temperature |
| Evaluation | Measurement of reflectance at 460 nm |

The results are expressed as ΔR=the difference in reflectance at 460 nm with and without the enzyme.

| Lipolytic enzyme | Dosage, LU/l | ΔR |
|---|---|---|
| SDL714 | 5000 | 7.1 |
| Lumafast | 1250 | 1.5 |
|  | 12500 | 0 |
| Lipomax | 1250 | 0.8 |
|  | 12500 | 1.2 |

The results show that SDL has a significant first-wash activity, whereas the two prior-art enzymes have almost no such effect, even when used at a much higher dosage.

ADVANTAGEOUS EFFECT OF THE INVENTION

The lipases having low temperature coefficients, lipases having high activity in the presence of bleaching agents, lipases having high stability in the presence of bleaching agents, and lipases having high activity in the presence of high concentration LAS of this invention can decompose and remove fats and oil contamination even at low temperatures, and use of detergent compositions containing the lipases enables an increase in the washing power of the detergent composition upon washing.

The lipases having an optimum pH of at least 11 (represented by SDL714 and SDL715) when contained in detergent compositions increase their washing effect.

Furthermore, *Pseudomonas stutzeri* SD711, SD712 and SD713 strains, Pseudomonas sp. SD714, SD715, SD716 and SD717 strains, *Acinetobacter baumanni* SD718 strain, bacterial strains bacteriologically equivalent to the eight strains, and variants thereof of this invention are useful in effectively producing the lipases of this invention. The lipases of this invention can be produced efficiently by the method for producing lipases according to this invention.

Figure 1:
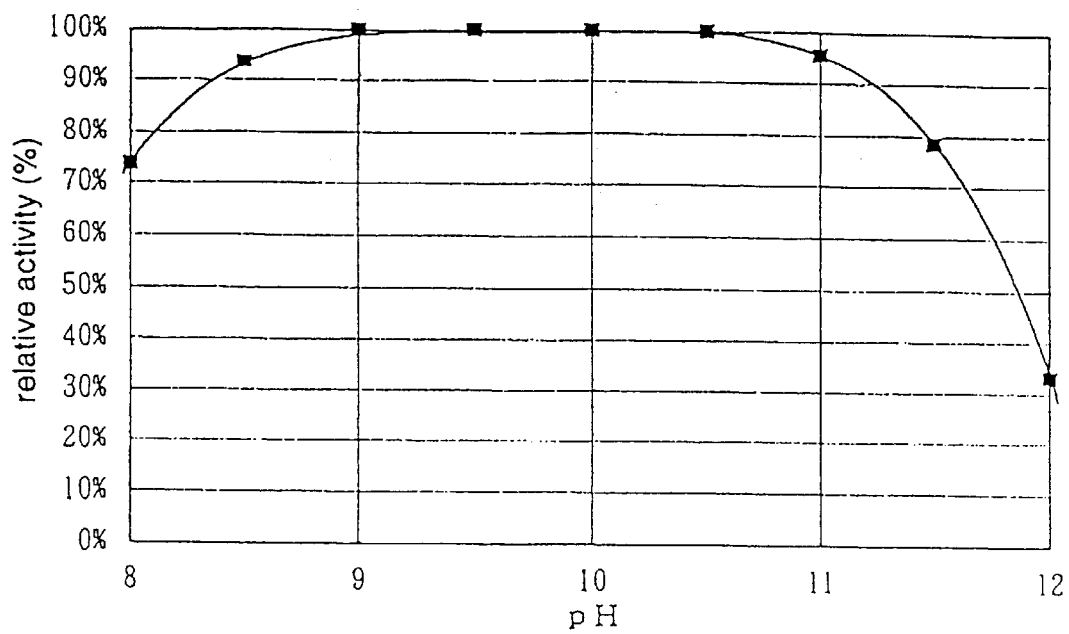
FIG. 1 is a pH profile of SDL711.
Figure 2:
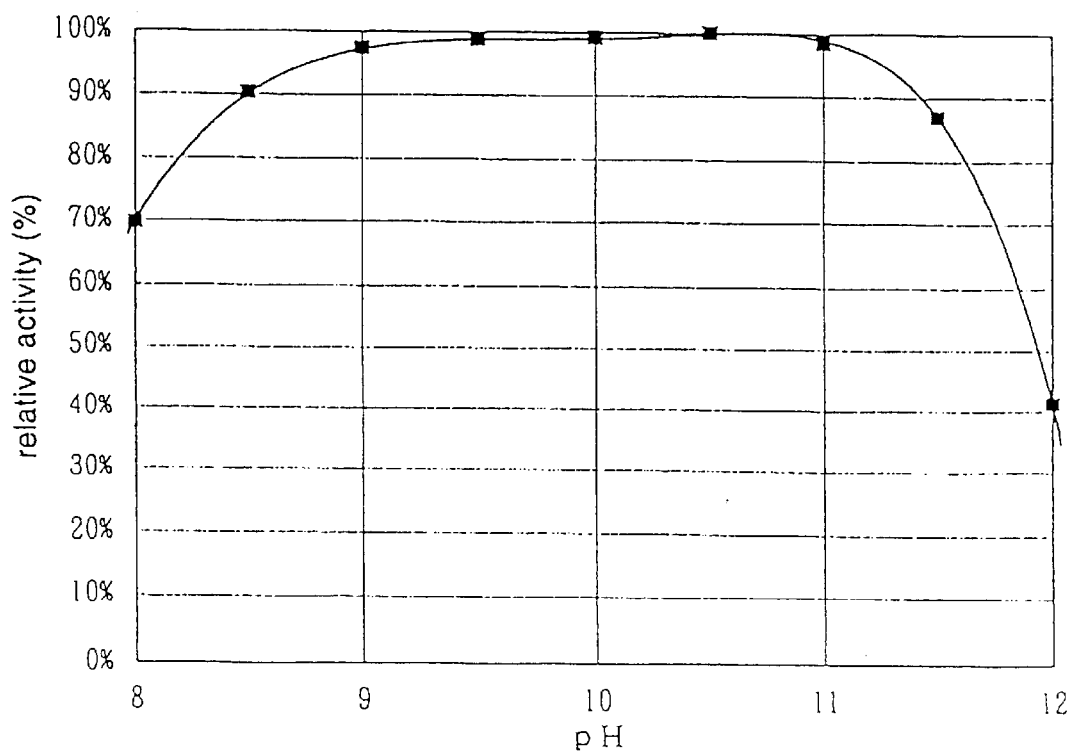
FIG. 2 is a pH profile of SDL712.
Figure 3:
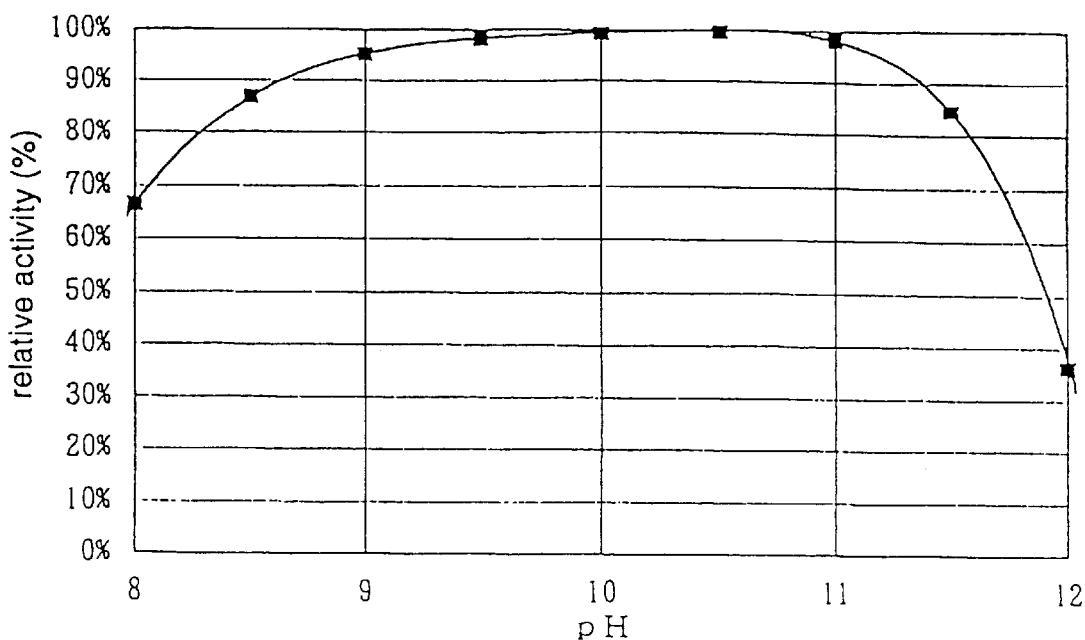
FIG. 3 is a pH profile of SDL713.
Figure 4:
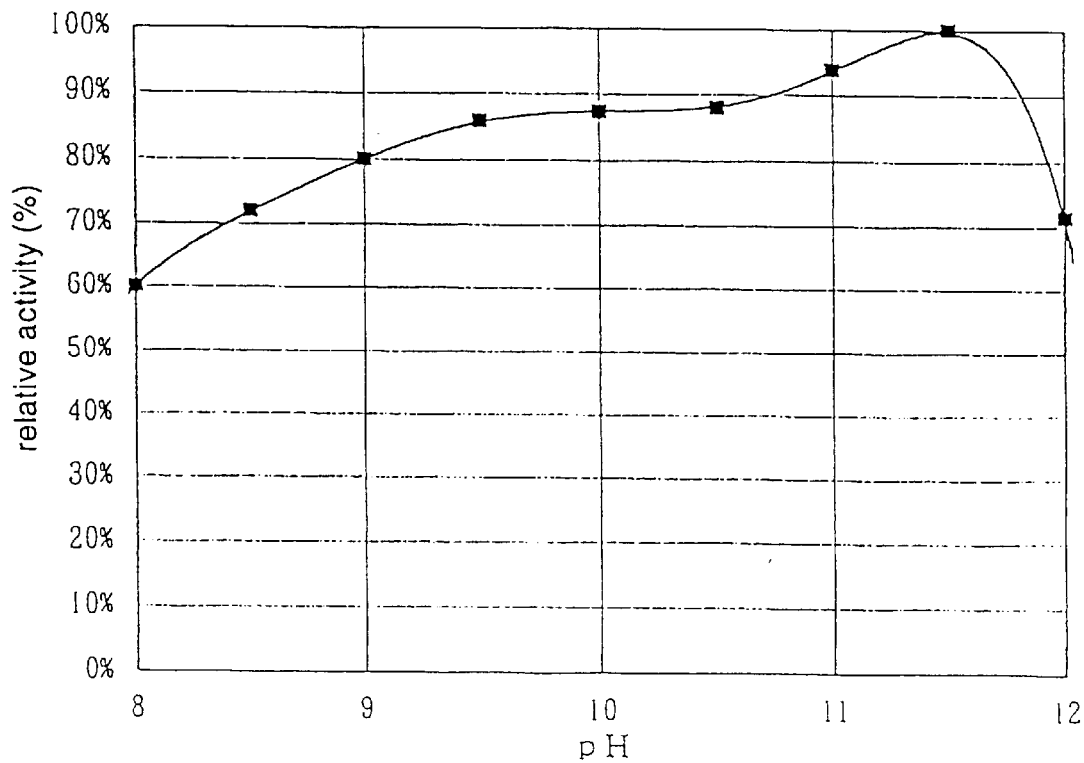
FIG. 4 is a pH profile of SDL714.
Figure 5:
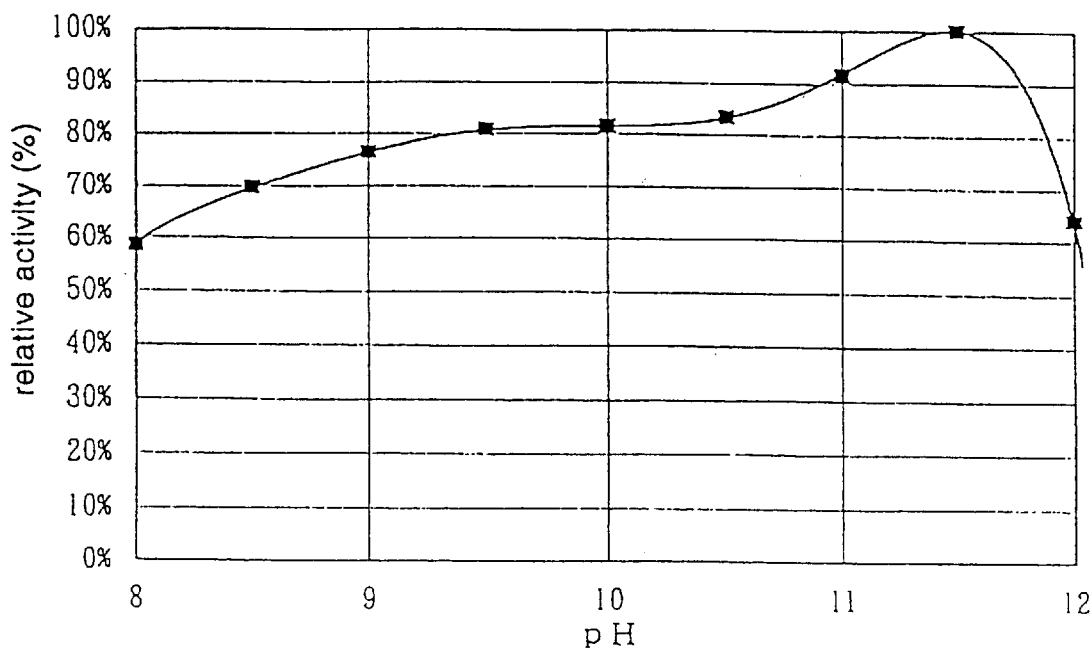
FIG. 5 is a pH profile of SDL715.
Figure 6:
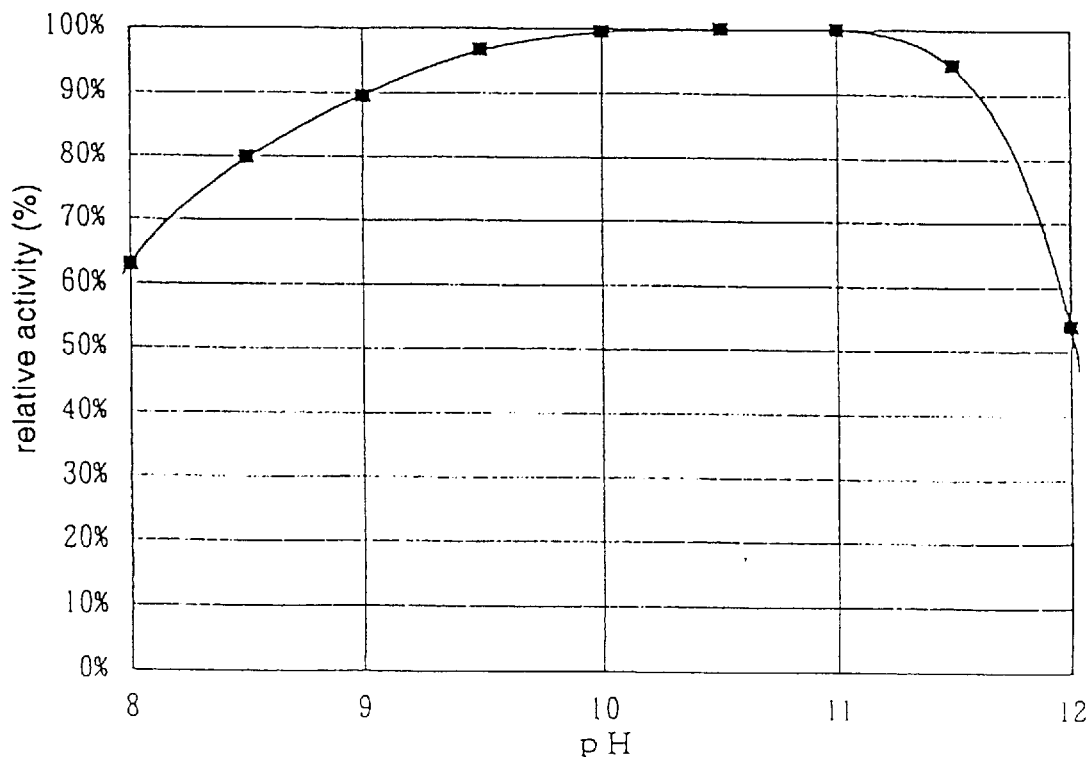
FIG. 6 is a pH profile of SDL716.
Figure 7:
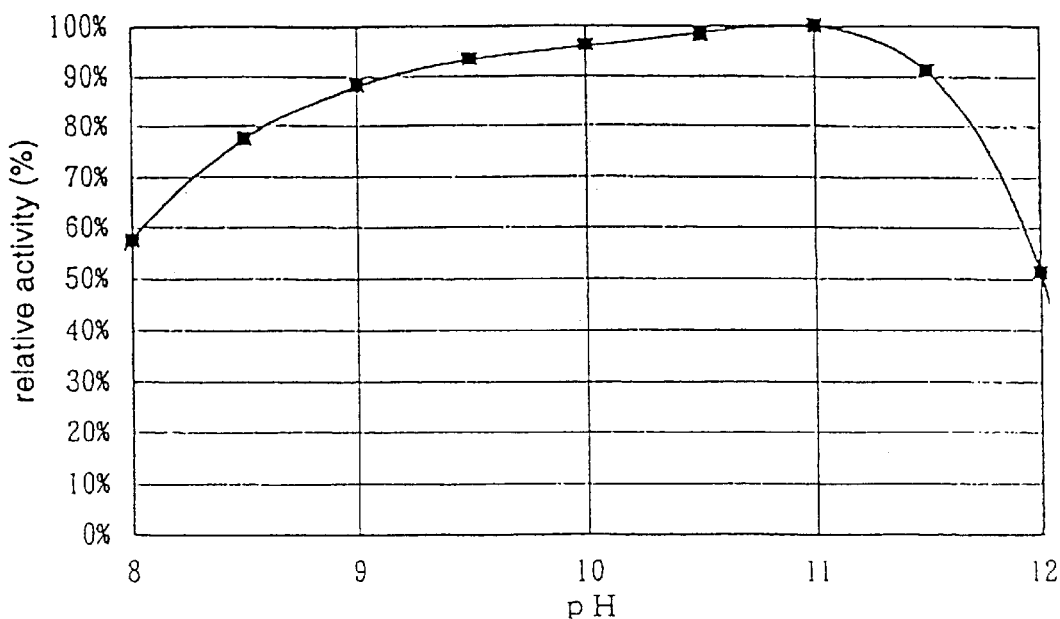
FIG. 7 is a pH profile of SDL717.
Figure 8:
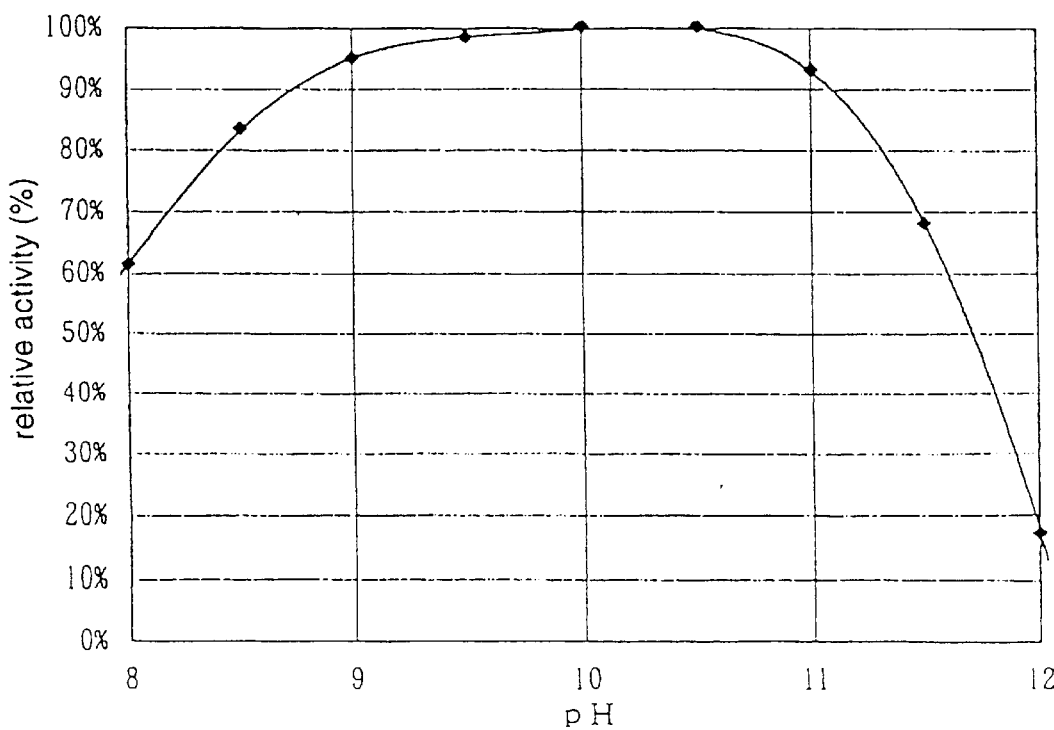
FIG. 8 is a pH profile of SDL718.
Figure 9:
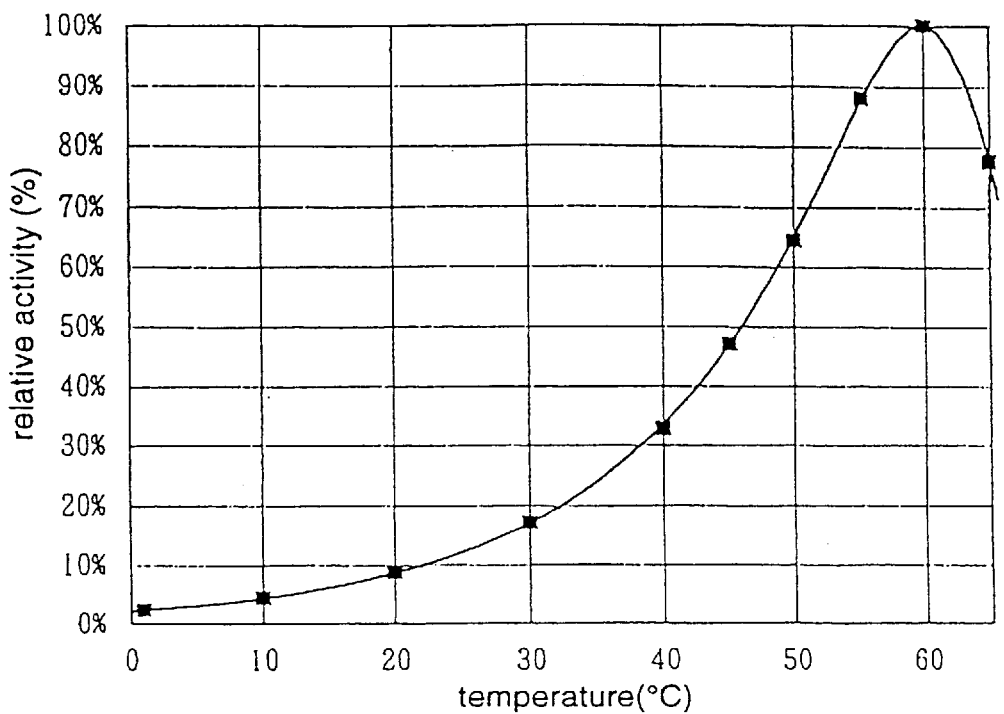
FIG. 9 is a temperature profile of SDL711.
Figure 10:
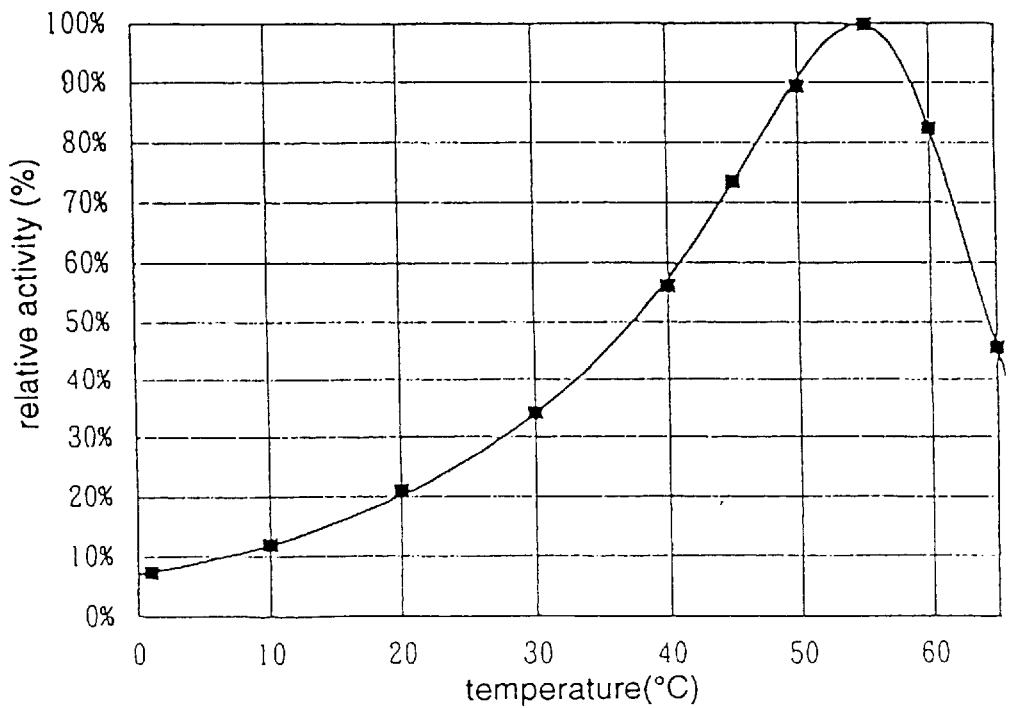
FIG. 10 is a temperature profile of SDL712.
Figure 11:
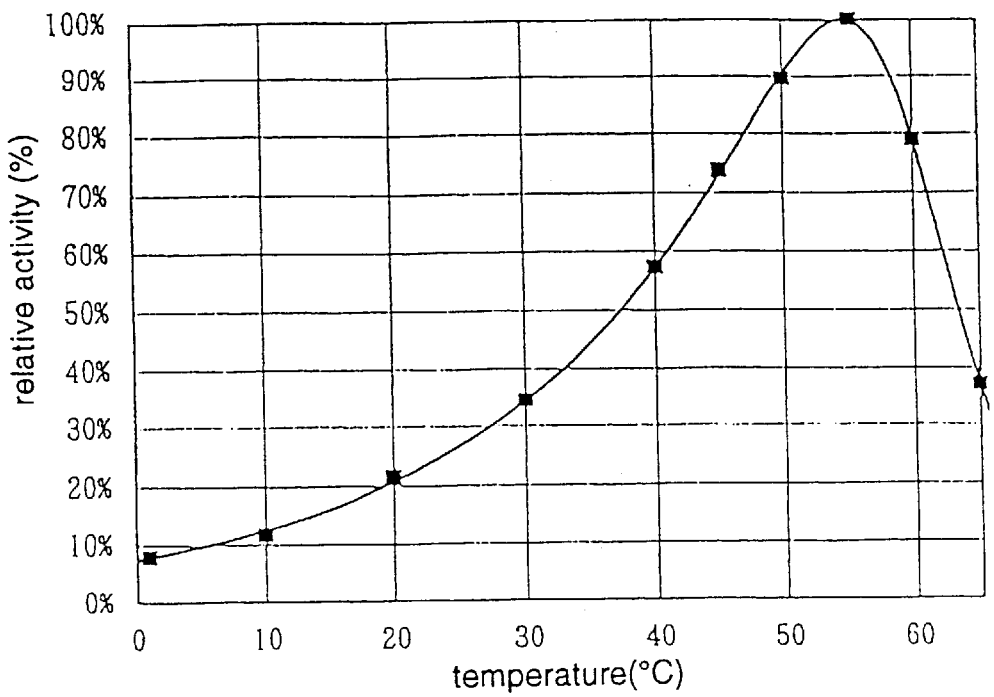
FIG. 11 is a temperature profile of SDL713.
Figure 12:
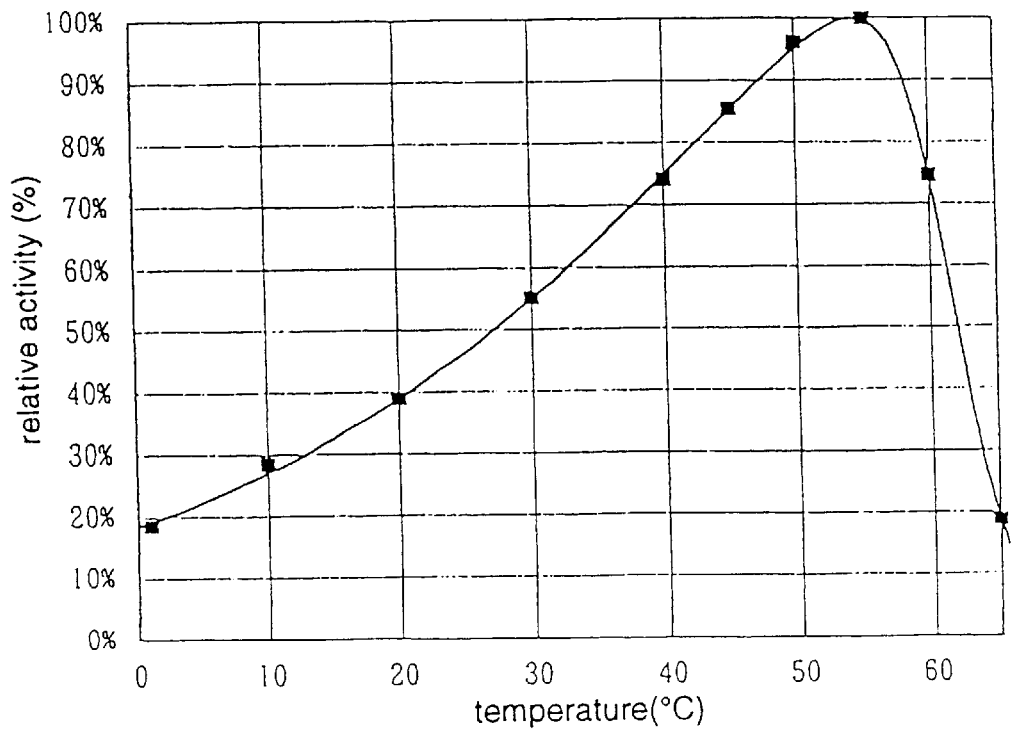
FIG. 12 is a temperature profile of SDL714.
Figure 13:
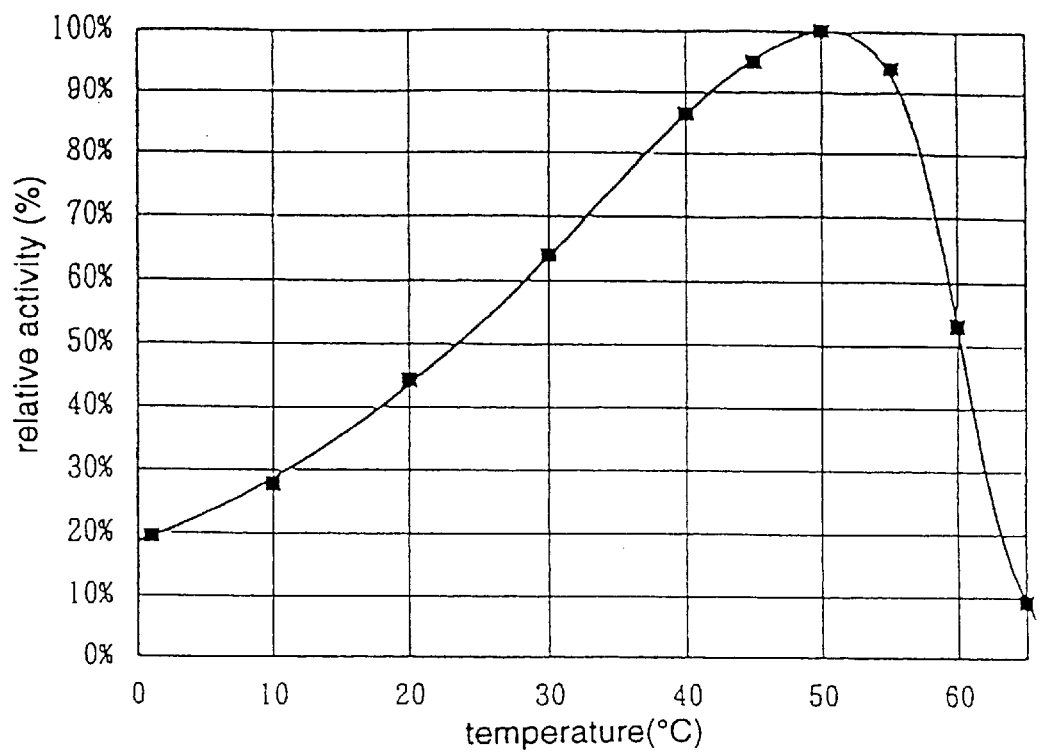
FIG. 13 is a temperature profile of SDL715.
Figure 14:
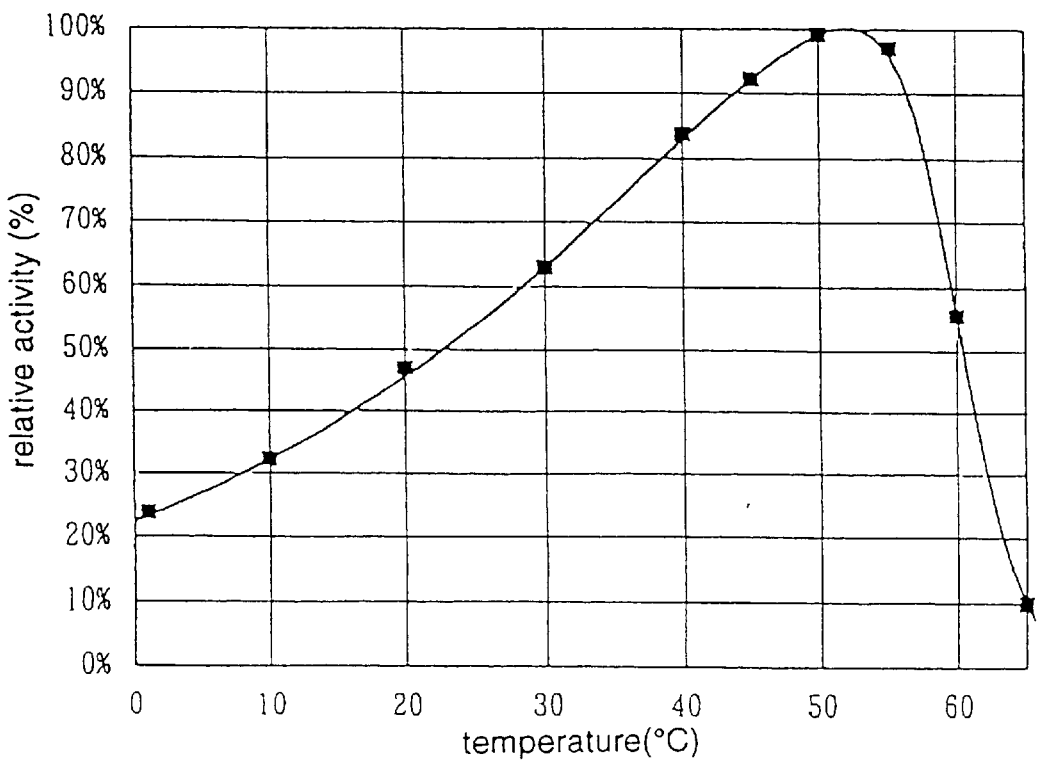
FIG. 14 is a temperature profile of SDL716.
Figure 15:
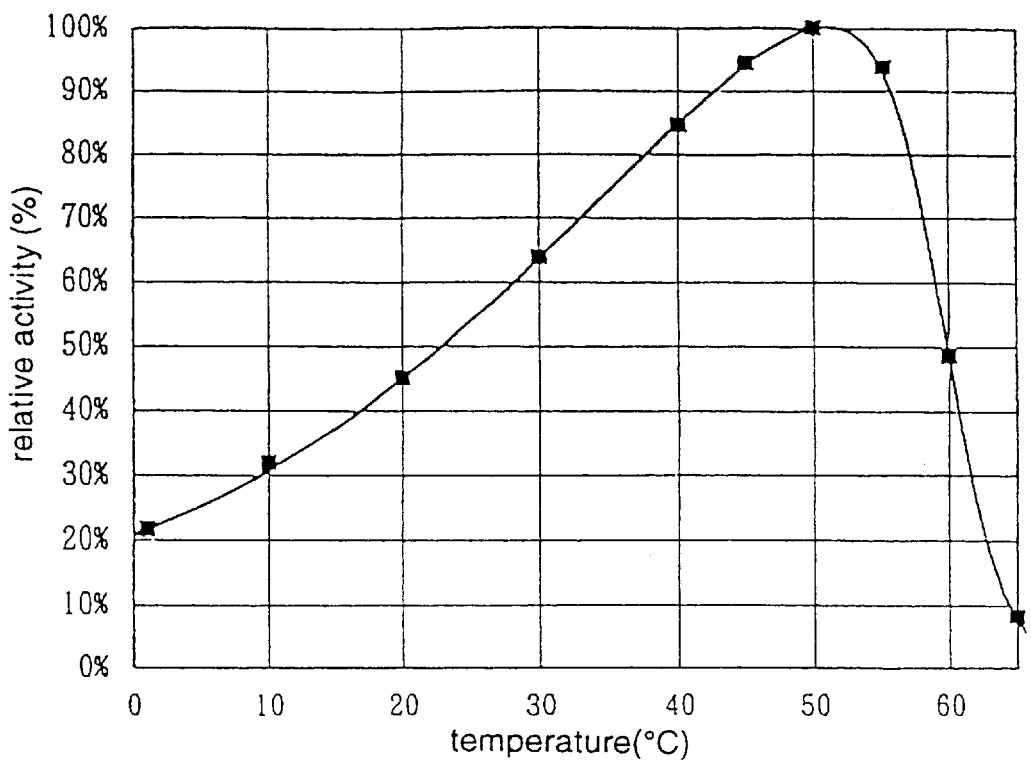
FIG. 15 is a temperature profile of SDL717.
Figure 16:
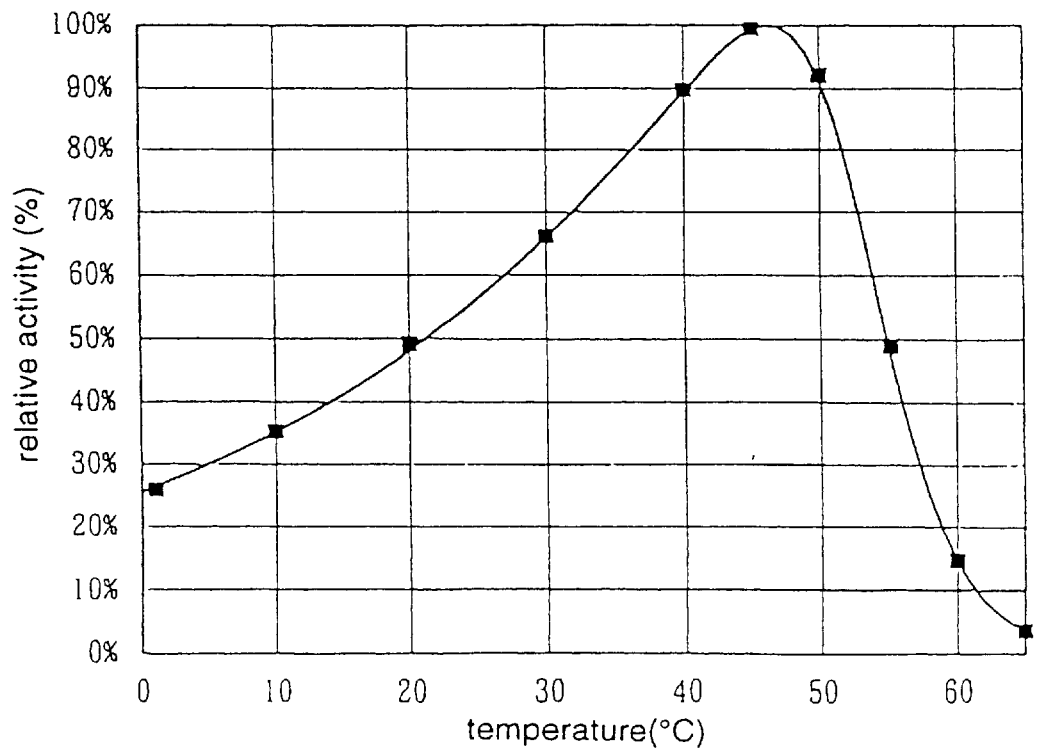
FIG. 16 is a temperature profile of SDL718.

What is claimed is:

1. A lipase obtained from *P. Stutzeri* strain SD711 (FERM BP-5892), SD712 (FERM BP-5893), or SD713 (FERM BP-5894); Pseudomonas sp. strain SD714 (FERM BP-5895), SD715 (FERM BP-5896), SD716 (FERM BP-5897), or SD717 (FERM BP-5898), or Acinetobacter, wherein said lipase has the following properties:
   a) an optimum temperature of at least 40° C.; and
   b) an activity at 1° C. which is at least 20% of the activity at 30° C.

2. A lipase obtained from *P. Stutzeri* strain SD711 (FERM BP-5892), SD712 (FERM BP-5893), or SD713 (FERM BP-5894); Pseudomonas sp. strain SD714 (FERM BP-5895), SD715 (FERM BP-5896), SD716 (FERM BP-5897), or SD717 (FERM BP-5898), or Acinetobacter, which has an activity measured in a solution containing 0.02% sodium linear alkylbenzene sulfonate (LAS) using an olive oil emulsion as a substrate which is at least 20% of the activity in the absence of LAS, and which has at least one of the following properties a) to c) below:
   a) a decomposition rate of p-nitrophenyl palmitate in a solution containing 0.046% LAS at 25° C. in the presence of 0.5% hydrogen peroxide of at least 80% of the decomposition rate in the absence of hydrogen peroxide;
   b) a residual activity after incubation in a solution containing 0.05% LAS and 0.55% hydrogen peroxide at 25° C. for 1 hour, which is at least 50% of the activity before the incubation; and/or
   c) a decomposition rate of p-nitrophenyl palmitate in a solution at 25° C. containing 0.2% LAS which is at least 50% of the decomposition rate in a solution containing 0.02% LAS.

3. A lipase obtained from *P. Stutzeri* strain SD711 (FERM BP-5892), SD712 (FERM BP-5893), or SD713 (FERM BP-5894); Pseudomonas sp. strain SD714 (FERM BP-5895), SD715 (FERM BP-5896), SD716 (FERM BP-5897), or SD717 (FERM BP-5898), or Acinetobacter and which has property a) and/or b) below:
   a) a decomposition rate of p-nitrophenyl palmitate in a solution at 25° C. containing 0.046% LAS in the presence of 0.5% hydrogen peroxide which is at least 80% of the decomposition rate in the absence of hydrogen peroxide; and
   b) a residual activity after incubation in a solution containing 0.05% LAS and 0.55% hydrogen peroxide at 25° C. for 1 hour, which it at least 50% of the initial activity before the incubation.

4. A lipase obtained from *P. Stutzeri* strain SD711 (FERM BP-5892), SD712 (FERM BP-5893), or SD713 (FERM BP-5894); Pseudomonas sp. strain SD714 (FERM BP-5895), SD715 (FERM BP-5896), SD716 (FERM BP-5897), or SD717 (FERM BP-5898), or Acinetobacter, which has the following properties:
- a) activity throughout a pH range of 8.0 to 2.0 and an optimum pH within a range of 8.5 to 12;
- b) activity throughout a temperature range of 1 to 65° C. and an optimum temperature within a range of 45 to 65° C.;
- c) a molecular weight of 30,000±3,500 as measured by SDS polyacrylamide gel electrophoresis.

5. The lipase of claim 4, which has the following properties:
- a) an optimum pH at about 11.5
- b) an optimum temperature at about 54° C.
- c) a molecular weight of 29,500±3,000 as measured by SDS-polyacrylamide gel electrophoresis.

6. The lipase of claim 4, which has the following properties:
- a) an optimum pH at about 11.5.
- b) an optimum temperature at about 50° C.
- c) a molecular weight of 29,500±3,000 as measured by SDS- polyacrylamide gel electrophoresis.

7. The lipase of claim 4, which has the following properties:
- a) an optimum pH at about 10 to 11.
- b) an optimum temperature at about 52° C.
- c) a molecular weight of 30,000±3,000 as measured by SDS-polyacrylamide gel electrophoresis.

8. The lipase of claim 4, which has the following properties:
- a) an optimum pH at about 11.
- b) an optimum temperature at about 51° C.
- c) a molecular weight of 30,000±3,000 as measured by SDS-polyacrylamide gel electrophoresis.

9. The lipase of claim 4, which has the following properties:
- a) an optimum pH at about 9 to 10.5.
- b) an optimum temperature at about 60° C.
- c) a molecular weight of 30,500±3,000 as measured by SDS-polyacrylamide gel electrophoresis.

10. The lipase of claim 4, which has the following properties:
- a) an optimum pH at about 9.5 to 11.
- b) an optimum temperature at about 55° C.
- c) a molecular weight of 30,000±3,000 as measured by SDS-polyacrylamide gel electrophoresis.

11. A bacterium belonging to the genus Acinetobacter which produces the lipase in claim 10.

12. A bacterium selected from the group consisting of *P. Stutzeri* strain SD711 (FERM BP-5892), SD712 (FERM BP-5893), or SD713 (FERM BP-5894); Pseudomonas sp. strain SD714 (FERM BP-5895), SD715 (FERM BP-5896), SD716 (FERM BP-5897), or SD717 (FERM BP-5898).

13. A lipase which has the following properties:
- a) an optimum temperature of at least 40° C.;
- b) an optimum pH greater than 11; and
- c) an activity at 1° C. which is at least 20% of the activity at 30° C.

14. A lipase of claim 13 which is obtained from a culture of a bacterium belonging to the genus Pseudomonas.

15. A lipase which has the following properties
- a) an optimum temperature of less than 55° C. but at least 40° C.; and
- b) an activity at 1° C. which is at least 20% of the activity at 30° C.

16. A lipase of claim 15 which is obtained from a culture of a bacterium belonging to the genus Pseudomonas or Acinetobacter.

* * * * *